(12) United States Patent
Cote et al.

(10) Patent No.: US 11,318,008 B2
(45) Date of Patent: May 3, 2022

(54) GASTROINTESTINAL IMPLANT DELIVERY SYSTEMS AND METHODS

(71) Applicant: GI Dynamics, Inc., Boston, MA (US)

(72) Inventors: Nicholas Cote, Somerville, MA (US); Ryan Hanlon, Hudson, NH (US); Ronald B. Lamport, Pelham, NH (US); Barry Maxwell, Spencer, MA (US); John Panek, Peabody, MA (US); Ian K. Parker, Bristol, RI (US); Scott Schorer, Duxbury, MA (US); Nicholas Williams, Sydney (AU)

(73) Assignee: GI Dynamics, Inc., Boston, MA (US)

( * ) Notice: Subject to any disclaimer, the term of this patent is extended or adjusted under 35 U.S.C. 154(b) by 116 days.

(21) Appl. No.: 16/073,652

(22) PCT Filed: Jan. 30, 2017

(86) PCT No.: PCT/US2017/015658
§ 371 (c)(1),
(2) Date: Jul. 27, 2018

(87) PCT Pub. No.: WO2017/132679
PCT Pub. Date: Aug. 3, 2017

(65) Prior Publication Data
US 2021/0205065 A1    Jul. 8, 2021

Related U.S. Application Data

(60) Provisional application No. 62/288,992, filed on Jan. 29, 2016.

(51) Int. Cl.
*A61F 2/04* (2013.01)
*A61F 2/95* (2013.01)
*A61F 5/00* (2006.01)

(52) U.S. Cl.
CPC .......... *A61F 2/04* (2013.01); *A61F 2/95* (2013.01); *A61F 5/0076* (2013.01);
(Continued)

(58) Field of Classification Search
CPC .............. A61M 5/00; A61F 2/04; A61F 2/95
See application file for complete search history.

(56) References Cited

U.S. PATENT DOCUMENTS 7,025,791 B2    4/2006 Levine et al.
7,122,058 B2    10/2006 Levine et al.
(Continued)

FOREIGN PATENT DOCUMENTS

| | | |
|---|---|---|
| EP | 2484316 A2 | 8/2012 |
| WO | WO-2013/023675 A1 | 2/2013 |
| WO | WO-2017/132676 A1 | 8/2017 |

OTHER PUBLICATIONS

International Search Report and Written Opinion for International Application No. PCT/US2017/015658, dated Apr. 4, 2017 (10 pages).
(Continued)

*Primary Examiner* — Jason-Dennis N Stewart
(74) *Attorney, Agent, or Firm* — Clark & Elbing LLP

(57) ABSTRACT

The present invention provides delivery systems for positioning a gastrointestinal implant in a patient, for example, for treatment of a metabolic disease. Also provided are methods for assembling the delivery systems, methods of positioning a gastrointestinal implant, and methods of treatment of metabolic diseases, such as type 2 diabetes, non-alcoholic steatohepatitis (NASH), non-alcoholic fatty liver disease (NAFLD), obesity, and related comorbidities thereof.

8 Claims, 16 Drawing Sheets

(52) U.S. Cl.
CPC ...... *A61F 5/0089* (2013.01); *A61F 2002/045* (2013.01); *A61F 2002/9511* (2013.01); *A61F 2220/0016* (2013.01); *A61F 2220/0025* (2013.01)

(56) References Cited

U.S. PATENT DOCUMENTS

| | | |
|---|---|---|
| 7,476,256 B2 | 1/2009 | Meade et al. |
| 7,608,114 B2 | 10/2009 | Levine et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,766,973 B2 | 8/2010 | Levine et al. |
| 7,771,382 B2 | 8/2010 | Levine et al. |
| 7,815,589 B2 | 10/2010 | Meade et al. |
| 7,815,591 B2 | 10/2010 | Levine et al. |
| 7,837,643 B2 | 11/2010 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,137,301 B2 | 3/2012 | Levine et al. |
| 8,162,871 B2 | 4/2012 | Levine et al. |
| 8,303,669 B2 | 11/2012 | Meade et al. |
| 8,376,981 B2 | 2/2013 | Laufer |
| 8,425,451 B2 | 4/2013 | Levine et al. |
| 8,628,583 B2 | 1/2014 | Meade et al. |
| 8,771,219 B2 | 7/2014 | Meade et al. |
| 8,834,405 B2 | 9/2014 | Meade et al. |
| 9,084,699 B2 | 7/2015 | Sue et al. |
| 9,095,416 B2 | 8/2015 | Meade et al. |
| 9,155,609 B2 | 10/2015 | Levine et al. |
| 9,173,760 B2 | 11/2015 | Belhe et al. |
| 9,237,944 B2 | 1/2016 | Meade et al. |
| 2006/0009858 A1 | 1/2006 | Levine et al. |
| 2008/0255587 A1 | 10/2008 | Cully et al. |
| 2012/0116286 A1 | 5/2012 | Williams et al. |
| 2013/0281911 A1 | 10/2013 | Babkes et al. |
| 2014/0194805 A1 | 7/2014 | Levine et al. |

OTHER PUBLICATIONS

Extended European Search Report for European Patent Application No. 17745093.9, dated Oct. 18, 2019 (9 pages).

Soft-tip Swab

Guidewire Hole

Removal Drawstring

Wave Anchor

GASTROINTESTINAL IMPLANT DELIVERY SYSTEMS AND METHODS

BACKGROUND OF THE INVENTION

According to the Center for Disease Control, 9.3% of the population of the United States has been diagnosed with type 2 diabetes or is predicted to develop type 2 diabetes, over half of whom are clinically obese. Type 2 diabetes and obesity can be broadly characterized as metabolic disorders, which often lead to life-threatening co-morbidities including non-alcoholic steatohepatitis (NASH), non-alcoholic fatty liver disease (NAFLD), hypertension, coronary artery disease, hypercholesteremia, sleep apnea, and pulmonary hypertension.

Patients suffering from metabolic diseases typically have an aberrant physiological response to ingested food after a meal. In particular, inadequate secretion of insulin has been associated with development of metabolic disorders such as type 2 diabetes. This blunted insulin response is caused by a loss or reduction of the "incretin effect," the gut-dependent secretion of incretins (e.g., hormones such as glucagon-like peptide-1 (GLP-1) and glucose-dependent insulinotropic polypeptide (GIP)). Thus, the modulation of signaling pathways in the gastrointestinal tract is emerging as a promising approach for treating metabolic disorders, such as type 2 diabetes, obesity, and related comorbidities.

Gastrointestinal implants, such as gastrointestinal sleeves, can treat metabolic disorders through incretin modulation by creating a barrier between ingested material (e.g., chyme) and a region of the gastrointestinal luminal wall (e.g., a region distal to the pylorus, e.g., duodenum and proximal jejunum). Delivery of such devices can be achieved using minimally-invasive endoscopic procedures. Existing delivery methods involve, after positioning the sleeve within the gastrointestinal tract, manually expanding the sleeve to its full length. This is performed by distally passing an inner catheter connected to the distal end of the sleeve through a stationary outer catheter connected to the proximal end of the sleeve. This expansion step introduces the potential for complication, such as jamming of the inner catheter.

Thus, there is a need in the field for a simplified delivery system and methods for placing a gastrointestinal implant within a patient's gastrointestinal system for treatment of metabolic disorders, such as type 2 diabetes, NASH, NAFLD, obesity, and related comorbidities thereof.

SUMMARY OF THE INVENTION

A simplified delivery system, which can be used to deliver various gastrointestinal implants (e.g., the existing ENDOBARRIER® gastrointestinal liner) is disclosed. The delivery system enables delivery of a gastrointestinal implant to the gastrointestinal tract (e.g., proximal duodenum, e.g., duodenal bulb), without extending the sleeve through the intestine prior to deployment of the anchor. Normal peristalsis and intestinal motility can be used to extend the sleeve, rather than manual extension, e.g., by an inner catheter. The invention also includes methods of assembling and using the delivery system, e.g., as a treatment for metabolic diseases.

In one aspect, the invention features a delivery system for placing a gastrointestinal implant in a gastrointestinal tract of a patient. The delivery system includes (a) a delivery catheter including a lumen; (b) a container assembly at the distal portion of the delivery catheter, the container assembly including a proximal capsule and a distal cap removably attachable thereto; and (c) a gastrointestinal implant. The gastrointestinal implant includes a sleeve configured to carry fluid (e.g., ingested material, e.g., chyme) from its proximal end to its distal end. Additionally or alternatively, the sleeve can be configured to carry secretions around the outside of the sleeve (e.g., biliary and pancreatic secretions, and/or other material e.g., from the stomach). An anchor, connected to the sleeve at or near its proximal end, is configured to secure the proximal end of the sleeve within the gastrointestinal tract. The gastrointestinal implant is configured to fit within the container assembly such that the anchor fits within the proximal capsule and all or a portion of the sleeve fits within the distal cap.

In another aspect, the invention provides a method of positioning a gastrointestinal implant in a patient. The method includes the steps of: (a) providing a container assembly containing a gastrointestinal implant including a proximal anchor and an elongate distal portion, wherein the container assembly comprises: (i) a proximal capsule containing the proximal portion of the gastrointestinal implant, and (ii) a distal cap containing all or part of the elongate distal portion; (b) directing the container assembly into the patient's gastrointestinal tract; (c) securing the proximal anchor to a luminal wall of the gastrointestinal tract; and (d) allowing peristalsis to extend the elongate distal portion. In some embodiments, step (c) is initiated by ejecting the gastrointestinal implant and the distal cap from the proximal capsule.

In another aspect, the invention provides a method of positioning a gastrointestinal implant in a patient, the method including the steps of: (a) providing a container assembly containing a gastrointestinal implant, the gastrointestinal implant having a proximal anchor and an elongate distal portion (e.g., a sleeve), wherein the container assembly includes: (i) a proximal capsule containing the proximal portion of the gastrointestinal implant, and (ii) a distal cap containing all or part of the elongate distal portion; (b) directing the container assembly into the patient's gastrointestinal tract; (c) ejecting the proximal anchor from the proximal capsule while the elongate distal portion is retained within the distal cap; and (d) allowing the proximal anchor to secure to a luminal wall of the gastrointestinal tract and allowing peristalsis to extend the elongate distal portion. In some embodiments, step (b) is performed using a delivery catheter. In some embodiments, the elongate distal portion (e.g., the sleeve) is not connected to a catheter. In some embodiments, the elongate distal portion (e.g., the sleeve) is not manually extended. For example, the elongate distal portion can be extended wholly or partially by the patient's natural peristalsis. In some embodiments, the delivery catheter is removed prior to full extension of the elongate distal portion (e.g. the sleeve).

In another aspect, the invention features a method of assembling a delivery system. The method includes the steps of: (a) providing a gastrointestinal implant having: a sleeve configured to carry fluid (e.g., ingested material or chyme) from its proximal end to its distal end and an anchor connected to the sleeve at or near its proximal end configured to secure the proximal end of the sleeve within the gastrointestinal tract; (b) inserting the anchor within a proximal capsule connected to a distal portion of a delivery catheter; (c) inserting a portion of the sleeve within a distal cap; and (d) attaching the proximal end of the distal cap to the distal end of the proximal capsule.

In another aspect, the invention features a method of treating a metabolic disorder or comorbidity thereof, the method comprising positioning any gastrointestinal implant described herein using a method of any of the preceding aspects. In some embodiments, the metabolic disorder is type 2 diabetes, non-alcoholic steatohepatitis (NASH), or obesity.

In some embodiments of any of the preceding aspects, the distal cap is attachable to the outer diameter of the distal end of the proximal capsule. The distal cap can be rounded for atraumatic delivery. For example, the distal cap can be hemispherical in shape or bullet-shaped. In some cases, the distal cap has a length from 10 mm to 100 mm (e.g., from 11 mm to 90 mm, from 12 mm to 80 mm, from 13 mm to 70 mm, from 14 mm to 60 mm, from 15 mm to 50 mm, from 16 mm to 40 mm, from 17 mm to 30 mm, or from 18 mm to 25 mm, e.g., about 20 mm). An alternative embodiment of a distal cap having an increased length is shown in FIG. 15. The distal cap can be hollow or semi-hollow, having one or more walls from 1 mm to 5 mm in thickness (e.g., from 1 mm to 1.5 mm, from 1.5 mm to 2.0 mm, from 2.0 mm to 2.5 mm, from 2.5 mm to 3.0 mm, from 3.0 mm to 3.5 mm, from 3.5 mm to 4.0 mm, from 4.0 mm to 4.5 mm, or from 4.5 mm to 5.0 mm).

In some embodiments, the length of the distal cap is about 20 mm. The distal cap can be atraumatic (e.g., made of an atraumatic material, e.g., silicone, e.g., 50 durometer silicone, or have an atraumatic shape or texture). The distal cap can include a hole (e.g., a guidewire hole) through which a guidewire is configured to pass.

In some embodiments, the container assembly is less than 30 mm in diameter. Thus, in some cases, the container assembly is less than 30 mm in width at one or more directions perpendicular to the longitudinal axis (e.g., diameter; e.g., less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, less than 10 mm, less than 9 mm, less than 8 mm, less than 7 mm, less than 6 mm, or less than 5 mm; e.g., from 5 mm to 30 mm, from 8 mm to 25 mm, from 10 mm to 20 mm, or from 12 mm to 15 mm in width at one or more directions perpendicular to the longitudinal axis (e.g., diameter)). In some embodiments, the container assembly or the proximal capsule is about 13 mm in diameter.

The container assembly can further include an anchor locking mechanism within the proximal capsule (e.g., an anchor locking mechanism including an anchor locking wire). Additionally or alternatively, the container assembly may further include an ejection mechanism, e.g., configured to eject the gastrointestinal implant from the proximal capsule. In some cases, the ejection mechanism comprises a plunger.

In some embodiments, the anchor is configured to be positioned distal to the patient's pylorus (e.g., at the duodenum, e.g., at the proximal duodenum, e.g., at the duodenal bulb). The anchor may be configured to exert an outward radial force on a duodenal bulb lumen. For example, the outward radial force can be at least 0.1 Newtons (N) at an anchor diameter of 25 millimeters (mm)(e.g., at least 0.11 N, at least 0.12 N, at least 0.13 N, at least 0.14 N, at least 0.15 N, at least 0.2 N, at least 0.25 N, at least 0.3 N, at least 0.35 N, at least 0.4 N, at least 0.45 N, at least 0.5 N, at least 0.6 N, at least 0.7 N, at least 0.8 N, at least 0.9 N, at least 1.0 N, or more, e.g., from 0.1 N to 0.2 N, from 0.2 N to 0.3 N, from 0.3 N to 0.4 N, from 0.4 N to 0.5 N, or more at an anchor diameter of 25 mm). In some embodiments, the anchor of the gastrointestinal implant has an average spring rate of at least 10 N per meter (N/m)(e.g., at least 10 N/m, at least 11 N/m, at least 12 N/m, at least 13 N/m, at least 14 N/m, at least 15 N/m, at least 20 N/m, at least 25 N/m, at least 30 N/m, at least 35 N/m, at least 40 N/m, or more, e.g., from 10 N/m to 15 N/m, from 15 N/m to 20 N/m, from 20 N/m to 25 N/m, from 25 N/m to 30 N/m, or more) over its range of motion.

In some embodiments of the invention, the anchor of the gastrointestinal implant is a wave anchor, and the proximal edge of the coupling liner matches the shape of the wave anchor (e.g., to form a "tulip" shape). In some embodiments, the wave anchor is a five-node sinusoidal wave anchor. The wave anchor can have a length from about 0.5 to about 2 inches (e.g., about 0.5 inches, about 0.6 inches, about 0.7 inches, about 0.8 inches, about 0.9 inches, about 1 inch, about 1.1 inches, about 1.2 inches, about 1.3 inches, about 1.4 inches, about 1.5 inches, about 1.6 inches, about 1.7 inches, about 1.8 inches, about 1.9 inches, or about 2 inches). In some embodiments, the wave anchor has a compressive elastic deformation diameter of 12 mm or less (e.g., from 5 to 12 mm, from 7 to 11 mm, or from 8 to 10 mm, e.g., about 11 mm, about 10 mm, about 9 mm, about 8 mm, about 7 mm, about 6 mm, about 5 mm, about 4 mm, about 3 mm, about 2 mm, or about 1 mm). In some cases, the wave anchor has a compressive elastic deformation of 30% or less (e.g., from 1% to 10%, from 10% to 20%, or from 20% to 30%, e.g., about 5%, about 10%, about 15%, about 20%, or about 25%). In some embodiments, the relaxed diameter of the wave anchor is at least 40 mm (e.g., at least 45 mm, at least 50 mm, at least 55 mm, at least 60 mm, at least 65 mm, or more).

The gastrointestinal implant can optionally include a drawstring connected to the anchor (e.g., the wave anchor), wherein the drawstring is configured to exert an inward radial force on a proximal portion of the wave anchor when pulled proximally.

In some embodiments, the diameter of the sleeve is substantially constant along its length. The sleeve can be substantially non-compliant. In some embodiments, the sleeve comprises an eversion-resistant element distal to the sleeve-coupling interface. In some cases, the sleeve is at least 40 cm in length (e.g., between 40 cm and 80 cm, e.g., about 60 cm in length). In some embodiments, the sleeve has a length of 12 inches, 13 inches, 14 inches, 15 inches, 16 inches, 17 inches, 18 inches, 19 inches, 20 inches, 21 inches, 22 inches, 23 inches, 24 inches, 25 inches, 26 inches, 27 inches, 28 inches, 29 inches, 30 inches, 31 inches, 32 inches, 33 inches, 34 inches, 35 inches, or 36 inches, e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm.

The sleeve can have a low coefficient of friction. For example, in some embodiments, the sleeve has a coefficient of friction of 0.3 or less.

BRIEF DESCRIPTION OF THE DRAWINGS

The following drawings are illustrative of particular embodiments of the present invention and are not limiting to various embodiments encompassed by the present invention.

FIG. 2A shows a flange extending radially at about 120° from a distal longitudinal axis. FIG. 2B shows a flange having an extension angle that becomes more acute along its radius. FIG. 2C shows a flange having an extension angle with an acute phase at its central radius and an obtuse phase at a distal radius.

DETAILED DESCRIPTION OF THE INVENTION

Figure 1:
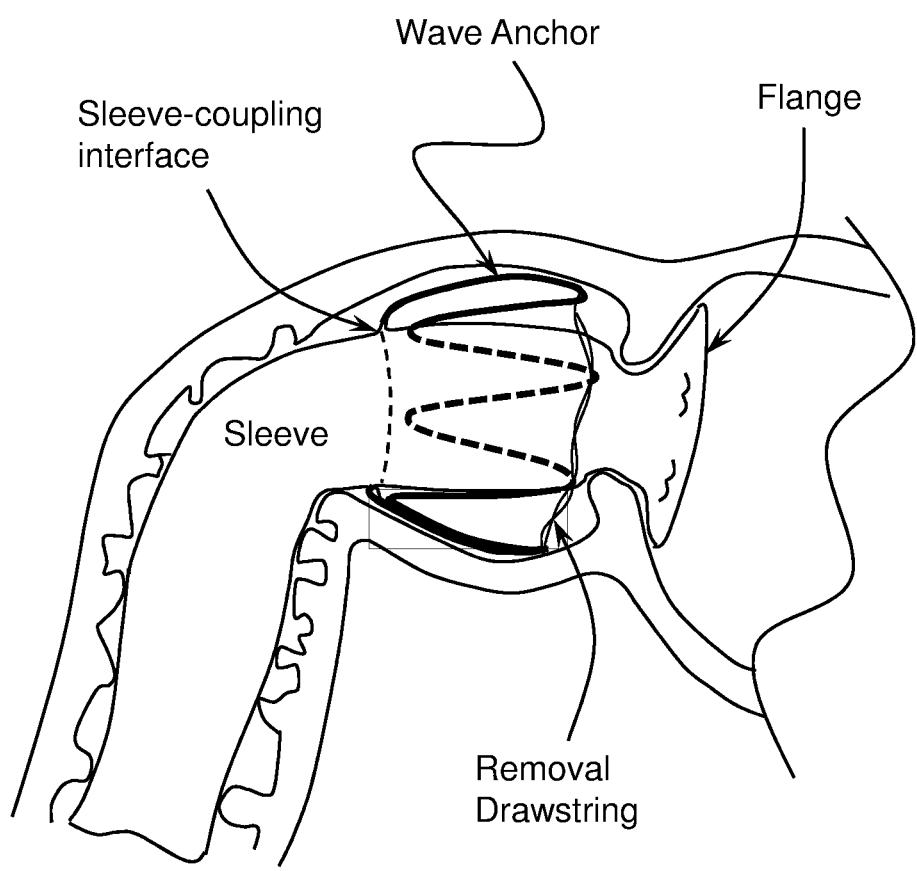
FIG. 1 is a drawing of a flanged gastrointestinal implant having a wave anchor positioned within a gastrointestinal tract.

The present invention provides delivery systems for positioning a gastrointestinal implant in a patient. The delivery systems of the present invention provide increases efficiency and reliability over current systems (e.g., by obviating the need to manually extend a gastrointestinal sleeve distally through a patient's duodenum and/or jejunum). Also provided are methods for assembling the delivery systems, methods of positioning a gastrointestinal implant using the delivery systems. The methods and delivery systems of the invention can be used for treatment of metabolic diseases, such as type 2 diabetes, non-alcoholic steatohepatitis (NASH), non-alcoholic fatty liver disease (NAFLD), obesity, and related comorbidities thereof.

Definitions

As used herein, the terms "gastrointestinal implant" includes an anchor for securely positioning the gastrointestinal implant to the stomach and a sleeve to limit absorption of nutrients in the duodenum. A "sleeve," as used herein, refers to a hollow, cylindrical gastrointestinal liner that is open at both ends and adapted to extend longitudinally within the duodenum. Fluid (e.g., partially digested food, chyme, or other endogenous or exogenous fluid) passing through the GI tract passes through the interior of the sleeve.

As used herein, an "anchor" refers to an annular element of a gastrointestinal implant that resists longitudinal motion (e.g., migration resulting from peristalsis or fluid shear forces) of the gastrointestinal implant by exerting a force against a gastrointestinal luminal wall. An anchor may resist motion of the gastrointestinal implant by exerting a radial force on an inward-facing gastrointestinal luminal wall, by exerting a proximal force on a distally-oriented gastrointestinal luminal wall, or by exerting a distal force on a proximally oriented gastrointestinal luminal wall. Anchors may or may not penetrate a gastrointestinal luminal wall. A "wave anchor" refers to an anchor having an undulating pattern along its longitudinal axis. Undulations can be sinusoidal.

To "secure" an anchor or a gastrointestinal implant refers to an act that results in the immobilization of the anchor or device at a position. For example, securing an anchor includes deploying an anchor such that the anchor expands to exert a force on the gastrointestinal wall, thereby immobilizing the anchor.

As used herein, to "exert a force" includes (a) transmitting a force, for example, from one region of the gastrointestinal tract to another (e.g., from a distal portion of the duodenal bulb to a distally-oriented surface of the pyloric sphincter) and (b) converting potential energy to force, for example, as occurs during radial expansion of a spring-like anchor against a gastrointestinal luminal wall.

As used herein, "relaxed" and "intrinsic" are used interchangeably to refer to the physical state of an element in an unconstrained environment. A "relaxed diameter" of an anchor refers to its natural or equilibrium diameter prior to loading into a catheter, in the absence of external force.

As used herein, the "compressive elastic deformation diameter" is the limit of diameter compression below which the anchor deforms and will not return to its original relaxed diameter or original relaxed shape. The compressive elastic deformation diameter can be characterized in absolute or relative terms.

As used herein, the term "about" refers to +/−10% of a recited value.

As used herein, the term "treatment" refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, the gastrointestinal implant is used to control metabolic disorders (e.g., type 2 diabetes, NASH, NAFLD, obesity, and related comorbidities). In some embodiments, removal of gastrointestinal implant is provided to delay development of a disease or to slow the progression of a disease.

As used herein, the terms "subject" or "patient" refer to any mammal (e.g., a human) having a gastrointestinal tract capable of containing of gastrointestinal implant of the invention. A patient who is being treated for a metabolic disorder, e.g., high blood sugar, diabetes (e.g., type 2 diabetes), obesity, NASH, NAFLD, or a related comorbidity thereof, may be one who has been diagnosed by a medical or veterinary practitioner as the case may be as having such a condition. Diagnosis may be performed by any suitable means. Patients of the invention may have been subjected to standard tests or may have been identified, without examination, as one at high risk of having or developing a metabolic disorder, e.g., type 2 diabetes, obesity, NASH, NAFLD, or a related comorbidity due to the presence of one or more risk factors, such as age, genetics, or family history.

As used herein, the term "comorbidity" or "related comorbidity" refers to one or more conditions, syndromes, diseases, or disorders that co-occur with metabolic disorders and can be either directly or indirectly linked to metabolic disorders. For example, metabolic disorder-related conditions may include type 2 diabetes, obesity, NAFLD, NASH, dyslipidemia, elevated serum/plasma LDL, elevated VLDL, elevated triglycerides, elevated cholesterol, plaque formation leading to narrowing or blockage of blood vessels, glucose intolerance, myocardial infarction, increased risk of hypertension/stroke, or coronary heart disease. As used herein, "diabetes mellitus type 2" or "type 2 diabetes" (also known as diabetes mellitus type 2, non-insulin-dependent diabetes (NIDDM), obesity-related diabetes, or adult-onset diabetes) refers to a metabolic disorder that is primarily characterized by insulin resistance, relative insulin deficiency, and hyperglycemia.

As used herein, the term "gastrointestinal," "GI," "gastrointestinal tract," or "GI tract" refer to the entire alimentary canal, from the oral cavity to the rectum (e.g., the tube that extends from the mouth to the anus, including, e.g., the esophagus, stomach, small intestine, large intestine, and rectum) in which the movement of muscles and release of hormones and enzymes digest food.

As used herein, the term "incretin" refers to a compound that directly or indirectly stimulates insulin release, inhibits glucagon release, and reduces gastric emptying. For example, incretins stimulate an increase in the amount of insulin released from the pancreas when plasma glucose levels are elevated relative to normal after food consumption, thereby leading to a decrease in blood glucose levels. Specific examples of incretins include gastric inhibitory peptide (i.e., glucose-dependent insulinotropic polypeptide, or GIP) and glucagon-like peptide-1 (GLP-1), along with their analogs and derivatives.

As used herein, "sleeve-coupling interface" refers to the point of the sleeve that is connected to anchor by a coupling liner. In some cases, the sleeve-coupling interface circumscribes the sleeve at a point along its length, e.g., at or distal to the distal end of the anchor.

Unless otherwise specified, a longitudinal axis refers to the longitudinal axis of the gastrointestinal tract (i.e., the line running through the gastrointestinal lumen equidistant from the luminal walls). It will be understood that, due to the tortuosity of the gastrointestinal tract, the directionality of its longitudinal axis and associated radial coordinates will vary along its length. For cases in which the "longitudinal axis of the device" is referred to, it is explicitly referred to as such.

The orientation of any surface (e.g., a luminal surface, luminal wall, or device surface) is characterized herein according to the direction of its normal line (i.e., a vector originating at and projecting orthogonally outward from its surface). As used herein, the orientation of a gastrointestinal luminal surface is an average of any micro features and is therefore independent of, e.g., microvilli.

The angle between a normal line and the longitudinal axis of a "proximally oriented" or a "distally-oriented" surface is $\geq 0°$ and $<90°$. For example, a "proximally oriented surface" of a lumen herein refers to a luminal surface that faces in a proximal direction (e.g., the stomach side of the pyloric sphincter), whereas a "distally-oriented surface" of a lumen herein refers to a luminal surface that faces in a distal direction (e.g., the intestinal side of the pyloric sphincter).

The term "pyloric orifice" refers to open area on the plane in which the pyloric opening lies.

The term "pyloric sphincter" refers to the tissue (e.g., epithelial and muscular tissue) that surrounds the pyloric orifice.

As used herein, "radial" refers to any direction that is substantially orthogonal to a reference longitudinal axis (e.g., the longitudinal axis of the anchor). For example, an inward radial force is exerted on a compressed anchor by inner walls of a catheter in which it resides. An outward radial force may be imparted, e.g., by an anchor upon expansion of its radius, e.g., from a radially compressed state to a radially expanded state (e.g., a relaxed or intrinsic state), against a luminal wall.

As used herein, a "flanged" element or a "flange" refers to a projection that, when implanted in a subject, wholly or partially extends radially (i.e., in a direction having a radial component from a longitudinal axis of a pyloric orifice (e.g., between 90° and 180° outward from the longitudinal axis of the pyloric orifice)) and configured to attach a gastrointestinal implant to a proximally oriented luminal surface (e.g., a proximal surface of the pyloric sphincter and/or an antral surface of the stomach).

As used herein, the term "fluid" refers to digested or partially digested material, for example chyme and digestive secretions.

In the event of any term having an inconsistent definition between this application and a referenced document, the term is to be interpreted as defined herein.

Gastrointestinal Implants

The systems and methods of the present invention involve gastrointestinal implants that limit contact and transfer of material across the luminal walls along a segment of the gastrointestinal tract (e.g., at the duodenum and/or upper jejunum). Gastrointestinal implants of the invention include a sleeve (e.g., a gastrointestinal sleeve, a bariatric sleeve, or a liner) and/or an anchor for resisting movement of the sleeve (e.g., proximal and/or distal movement of the liner within a gastrointestinal tract). For example, gastrointestinal implants of the invention include ENDOBARRIER® and adaptations or improvements thereof, such as a transpyloric device and/or devices including a flange (e.g., a flanged gastrointestinal implant described in U.S. Provisional Application No. 62/289,100, incorporated herein by reference).

Flanges

Gastrointestinal implants of the invention include, but are not limited to, those that feature a flanged proximal end for attaching the device to tissue of the pyloric sphincter (e.g., a proximal surface of the pyloric sphincter) and/or the antral surface of the stomach. By attaching to a proximally oriented tissue surface, a flange can guide fluid (e.g., chyme) from the stomach into the sleeve while providing resistance to distal migration of the gastrointestinal implant, e.g., as a result of peristalsis. In some cases, a flange obviates the need for a barbed anchor. For example, the present invention provides devices that resist distal migration by attachment of a flange at a proximal region (e.g., proximal to the pyloric orifice) and resist proximal migration by physical constraint of an anchor at a distal region (e.g., distal to the pyloric orifice, e.g., within the duodenal bulb). Such a device is shown in FIG. 1. In another example, the present invention provides devices that resist distal migration by attachment of a flange at a proximal region (e.g., proximal to the pyloric orifice) and resist proximal migration that by an eversion resistant sleeve that resists proximal eversion (e.g., aberrant proximal movement through the pyloric orifice that may cause obstruction to the flow of fluid). Eversion resistant sleeves are described in U.S. Pat. No. 7,766,973, which is herein incorporated by reference.

In general, a flange is attached to a proximal portion of the sleeve. In some cases, the flange defines the proximal opening of the sleeve (e.g., as a circular "rim" or "skirt" connected to the proximal end of the sleeve). In some embodiments, the flange extends radially in all directions from the sleeve, which may help prevent fluid from passing around the outside of the proximal end of the sleeve. The outer diameter of the flange may be constant (e.g., substantially circular). In such cases, the outer diameter of the flange can be at least 10% greater than the diameter of all or a portion of the sleeve (e.g., at least 10% greater than, at least 20% greater than, at least 30% greater than, at least 40% greater than, at least 50% greater than, at least 60% greater than, at least 70% greater than, at least 80% greater than, at least 90% greater than, at least 100% greater than, at least 150% greater than, at least 200% greater than, at least 250% greater than, at least 300% greater than, at least 400% greater than, or at least 500% greater than the diameter of all or a portion of the sleeve (e.g., the proximal end of the sleeve)). In some embodiments, the length of the sleeve extending from the distal end of the flange to the proximal end anchor is about 1 cm, about 2 cm, about 3 cm, about 4 cm, about 5 cm, about 6 cm, about 7 cm, about 8 cm, about 9 cm, or about 10 cm. In some cases, the length of the sleeve extending from the distal end of the flange to the proximal end of the anchor is 3 cm. In other cases, the length of the sleeve extending from the distal end of the flange to the proximal end of the anchor is 6 cm. The hole in the flange can be suitable to accommodate the diameter of the sleeve (e.g., from 1 to 3 cm, e.g., about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, or about 3.0 cm). In some cases, the flange has a hole (e.g., a central hole) that meets the proximal opening of the sleeve having a diameter of 2 cm.

Alternatively, the flange may extend radially at different lengths around the circumference of the sleeve (e.g., its outer diameter may be variable, e.g., ovoid or irregularly shaped). Such a configuration may be adapted for an asymmetric anatomy and/or physiological forces (e.g., at the pylorus or antrum of the stomach). Additionally or alternatively, an irregularly shaped outer diameter of a flange may serve to optimize the seal of the flange to the gastrointestinal wall. For example, the outer edge (e.g., outer diameter) of a flange may undulate (e.g., similarly to a sinusoidal wave anchor) to maintain contact to a dynamic luminal wall, e.g., to a bowl-shaped antral wall.

Figure 2A:
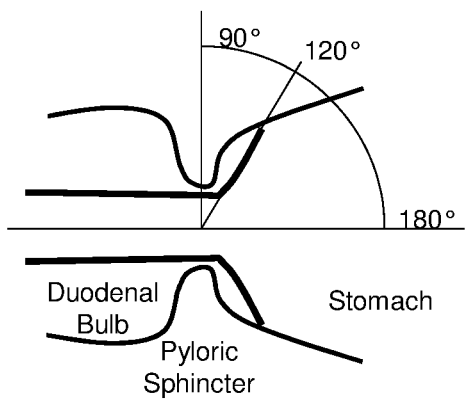
FIGS. 2A-2C are diagrams showing various angles of flange extension.
Figure 2B:
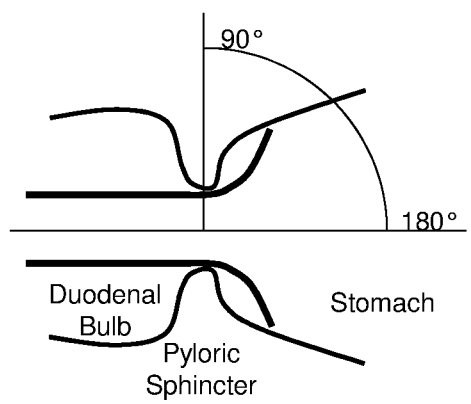
Figure 2C:
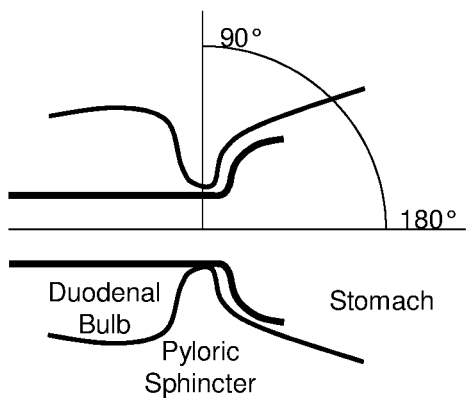

When in position in a subject, a flange extends, wholly or partially, in a direction having a radial component from a longitudinal axis of a pyloric orifice (e.g., between 90° and 180° outward from the longitudinal axis of the pyloric orifice). In some cases, all or most of the flange intrinsically extends radially between 90° and 180°, e.g., at about 100°, about 110°, about 120°, about 130°, about 140°, about 150°, about 160°, or about 170° outward from the longitudinal axis of the pyloric orifice, e.g., the angle of extension is substantially linear along the radius of the flange. In some cases, all or most of the flange intrinsically extends radially at about 120° outward from the longitudinal axis of the pyloric orifice (e.g., the distal longitudinal axis), as shown in FIG. 2A. Alternatively, the flange may extend at angle that varies along its radius. For example, the angle may become more acute as along the radius of the flange, such as shown in FIG. 2B. The angle may also vary in opposing directions over its radius. For example, a flange may become more acute at a central region and gradually become more obtuse (e.g., bowl-shaped) at a greater radius, as shown in FIG. 2C. It will be understood that, once attached to a proximally oriented surface proximal to the pyloric orifice, the angle of extension of the flange will substantially match that of the surface to which it is attached.

Suitable materials for flanges of the present invention include polymeric liners, such as polytetrafluoroethylene (PTFE), expanded PTFE (ePTFE), fluorinated ethylene propylene (FEP), perfluoroalkoxy (PFA), ethylene tetrafluoroethylene (ETFE), and polyvinylidene fluoride (PVDF). The flange can be an extension of the sleeve material (e.g., integrally formed), and it may have a greater thickness than all or a portion of the remainder of the sleeve. The thickness of the flange will depend on its attachment means.

Flanged gastrointestinal implants may feature a coupling liner that connects that connects to the sleeve at a sleeve-coupling interface. The coupling liner can be fastened to the sleeve by mechanical and/or chemical bonding, soldering, welding, and/or using other mechanical attachment means know in the art. The sleeve can be within the anchor. The sleeve can be fastened to the anchor by mechanical and/or chemical bonding, soldering, welding, and/or using other mechanical attachment means know in the art. In other embodiments, the present invention provides a gastrointestinal implant featuring a coupling liner that connects the anchor to the sleeve at a sleeve-coupling interface. The coupling liner can be fastened to the anchor by mechanical and/or chemical bonding, soldering, welding, and/or using other mechanical attachment means know in the art. In some embodiments, the coupling liner includes two layers of material. A first outer layer covers the exterior of the anchor, and a second inner layer covers the interior surface of the anchor. A drawstring may be threaded through the anchor and/or the coupling liner.

Alternatively, the coupling liner may be integrally formed with the sleeve. In some cases, the coupling liner is attached to the sleeve completely to form a seal around the circumference of the sleeve, e.g., to prevent passage of material longitudinally around the outside of the sleeve. In some embodiments, the coupling liner prevents retrograde passage of fluid.

In some embodiments, the coupling liner is wholly or partially made of the same material as the sleeve. The coupling liner can be wholly or partially made of PTFE, ePTFE, FEP, PFA, ETFE, or PVDF.

A flange can be attached to a sleeve by any suitable means known in the art. In some cases, the proximal end of the sleeve is cut longitudinally at one or more points along its circumference, creating strips of sleeve material, which can be splayed out and attached to a flange. In some embodiments, these portions of the sleeve can be sandwiched between two flange pieces. The two flange pieces (e.g., donut-shaped portions of PTFE/FEP) can then be attached to one another, for example, by hand soldering, to entrap the sleeve portions therebetween such that the sleeve lumen passes through the holes in the flange. Other methods of attaching the flange to the sleeve are known in the art.

Anchors

Gastrointestinal implants of the invention are configured to be retained within the gastrointestinal tract (e.g., within the duodenum, e.g., within the duodenal bulb) using one or more annular anchors, which resist longitudinal motion of the device through the gastrointestinal tract by exerting a force against a gastrointestinal luminal wall. In some embodiments, an anchor works in tandem with a flange to resist longitudinal migration, i.e., the anchor resists proximal migration while the flange resists distal migration.

The anchor can be attached to sleeve by any means suitable to longitudinally tether the sleeve to the anchor (e.g., to prevent longitudinal motion of the sleeve relative to the anchor). In some cases, the sleeve is directly attached to the anchor (e.g., at the proximal edge of the sleeve). In some cases, the anchor is enveloped by, or sandwiched between, layers of the sleeve.

In cases in which the sleeve includes a flange, the anchor can be connected to the sleeve by a coupling liner. The coupling liner may be the same or a similar material to that of the sleeve and projects from the sleeve at a sleeve-coupling interface, which forms the point of connection between the anchor and the sleeve. In cases in which the sleeve runs longitudinally through the center of the anchor, the coupling liner may connect to the sleeve around the full circumference of the sleeve. For example, the coupling liner may connect the anchor to the sleeve at a point on the sleeve that is at or distal to (e.g., less than 1 inch distal to) the distal end of the anchor. Such a configuration, in which the sleeve-coupling interface is beyond the overlapping anchor, may allow for radial displacement (e.g., partial collapse) of the anchor without substantially collapsing the sleeve (e.g., at or proximal to the sleeve-coupling interface). The anchor can be distal to the flange and proximal to all or a majority of the sleeve. In some cases, the sleeve runs longitudinally through the anchor (e.g., such that the anchor is coupled to the sleeve at a point that divides the sleeve into a proximal portion and a distal portion). Thus, the relaxed diameter of the anchor may exceed a maximum diameter of all or a portion of the sleeve (e.g., by between 10% and 200%, e.g., by 10%, 20%, 30%, 40%, 50%, 60%, 70%, 80%, 90%, 100%, 110%, 120%, 130%, 140%, 150%, 160%, 170%, 180%, 190%, 200%, or more). In some cases, the anchor may exert an outward radial force on all or a portion of the sleeve (e.g., to maintain the sleeve in an open or partly open position) and/or the gastrointestinal wall (e.g., at the duodenal bulb).

A suitable anchor of the present gastrointestinal implant can be a wave anchor, characterized by an undulating pattern along its longitudinal axis. Wave anchors are known in the art and described, for example, in U.S. Pat. Nos. 7,608,144, 8,137,301, 8,162,871, 9,155,609, 7,695,446, 7,678,068, 7,476,256, 7,682,330, 7,981,163, 8,834,405, 9,237,944, 7,815,589, 8,303,669, 8,628,583, 9,084,699, 7,976,488, and 8,425,451, each of which are incorporated herein by reference. In embodiments featuring a wave anchor, the coupling liner can be connected to the sleeve analogously to the connection of the wave anchor to the sleeve in any of the aforementioned references. For example, the coupling liner may be cut back to match the undulating shape of the wave anchor, such that the proximal edge of the coupling liner matches the shape of the wave anchor (e.g., forming a "tulip" shape). Such a configuration can facilitate the formation of a seal at the wave anchor, because proximal ends of the different "petals of the tulip" can flex independently as the coupling material does not restrain them. Additionally, the tulip-shaped proximal end, when installed, forms a secure seal along its entire perimeter when implanted in the gastrointestinal tract. Advantageously, such a tailored fit leaves no unsupported material between the edges of the device, behind which ingested material could be entrapped.

Suitable anchors can be manufactured from a resilient metal such as a heat-treated spring steel, stainless steel, or from an alloy such as nitinol (NiTi). Anchors, such as wave anchors, can be made from nitinol wire (e.g., from 0.01" to 0.03" nitinol wire). For example, Anchors up to 60 mm diameter have been fabricated from 0.023" Nitinol wire (see, e.g., U.S. Pat. No. 8,425,451). The wire diameter of the anchor can be adjusted to provide the desired force. Typically, shorter anchors use thinner wires. For example, a 19 mm long anchor was made from 0.016" diameter wire to provide the same compliance as the 32 mm long anchors shown (Id.). As the diameter of the wire becomes larger, the compressive elastic deformation diameter increases.

Other alloys include nickel-cobalt-chromium-molybdenum alloys possessing a unique combination of ultrahigh tensile strength, such as MP35N. Additionally, the anchor can be formed from a polymer and/or a composite having similar properties. The anchor can be manufactured from a single strand, such as a wire, contoured into the desired shape. Alternatively, the disclosed anchor can be manufactured from multi-strands of the same or different materials similarly contoured to the desired shape. In some embodiments, a wave anchor can be cut into the wave shape from tubular stock of the desired material, such as nitinol.

In some cases, the anchor includes attaching means adapted to secure the anchor to the gastrointestinal tract (e.g., the duodenum, e.g., the duodenal bulb). The attaching means can include an interference fit, chemical fasteners, mechanical fasteners, or the like. For example, the anchor can be attached to the surrounding anatomy using an interference fit provided by the relative size of the anchor in relation to the surrounding anatomy. Alternatively or in addition, the anchor can be attached to the surrounding anatomy using chemical fasteners, such as surgical adhesives. Mechanical fasteners can include, for example, sutures, surgical staples, barbs, or the like. In some embodiments, the mechanical fasteners can be dissolvable, dissolving after a predetermined time and allowing the device to pass naturally. Mechanical fasteners can include barbs that extend from the exterior surface of the anchor for anchoring the proximal portion of the sleeve to the muscular tissue of the surrounding anatomy. The barbs may be bi-directional for anchoring the proximal portion of the flexible sleeve to the intestine. Barbs may be bi-directional and aligned with the peristaltic axis of the gastrointestinal tract, i.e., some barbs are pointed in the direction of forward peristalsis to secure the anchor against forward motion through the gastrointestinal tract, and some barbs are pointed opposite the direction of forward peristalsis, to secure the anchor against reverse motion in the gastrointestinal tract. Typically, the barbs secure the anchor to muscular tissue of the intestine. In various embodiments, the barbs extend from the surface exterior surface of the anchor by about 2 mm or greater.

In other cases, the anchor is configured to provide adequate longitudinal support without the need for barbs (e.g., by sharing some of the forces with the flange of the present device). Accordingly, these gastrointestinal implants feature anchors that are not configured to puncture a gastrointestinal lumen.

The effects of varying the mechanical properties of various anchor designs have been studied and reported, for example, in U.S. Pat. No. 8,425,451, which is incorporated herein by reference. In general, it is believed that the stiffness or compliance of the anchor can determine the ability of the device seal against the tissue and to maintain any attaching means, e.g., barbs engaged in the tissue. The anchor should be sufficiently elastic to permit loading and delivery in a small capsule (e.g., max outer diameter of 16 mm, practical inner diameter of 12 mm) for implantation, followed by full expansion into the intestine. The diameter of the device should also be able to accommodate the full natural dilation of the tissue. Thus, the relaxed diameter of the anchor may be greater than 30 mm (e.g., greater than 35 mm, greater than 40 mm, greater than 45 mm, greater than 50 mm, greater than 55 mm, or greater than 60 mm). If the compliance of the anchor is too high (too soft), the anchor may separate from the tissue and cause leaks and/or migrations. If the anchor compliance is too low (too stiff), it may cause irritation to the tissue and/or require a larger capsule for delivery to avoid compressing beyond its elastic deformation diameter. Generally, the more nodes included in the undulating wave pattern, the more compliant the device will be. Additionally, the larger the filament or wire diameter, the less compliant the device will be. In some embodiments, such as laser-cut devices, both the width and thickness of the wire (e.g., rectangular profile) can be varied. Thus, the overall compliance of the device is determined at least from the wave pattern and the wire shape and/or diameter. In some embodiments, the wave anchor has at least four nodes (e.g., five, six, seven, eight, nine, or more nodes).

In various embodiments, the anchor is characterized by a radial force of about 0.1 Newtons (N) or greater at a compressed diameter of 25 mm. In some cases, the radial force at 25 mm compression is about 0.3 N or greater, e.g., about 0.4 N or greater, or between about 0.5 N and about 1.5 N. Additionally or alternatively, the anchor may characterized by an average spring rate of about 13 N per meter (N/m) or greater in a range of motion, the range of motion being within a diameter range defined by a relaxed diameter and a compressive elastic deformation diameter. More particularly, the average value of the spring rate may be between about 15 N/m and about 35 N/m. In some embodiments, the spring rate is substantially constant over the range of motion, i.e., the force versus displacement data is substantially linear over the range of motion.

Additionally or alternatively, the anchor may be characterized by a radial force over the range of motion of about 0.1 N or greater, e.g., about 0.2 N or greater, about 0.3 N or greater, or about 0.4 N or greater.

In some embodiments, the range of motion is about 20 mm or greater, e.g., about 30 mm or greater, or about 35 mm or greater. The range of motion can be a percentage of the relaxed diameter of the anchor of about 30% or greater.

The anchor may also be characterized by a relaxed diameter. Generally, the relaxed diameter can be about 40 mm or greater, e.g., about 45 mm or greater, or between about 45 mm and about 65 mm. In particular embodiments, the relaxed diameter is about 50 mm or about 60 mm.

An anchor can have a radial force being about 0.4 N or less at a diameter of 55 mm, e.g., at a diameter of 50 mm, 45 mm, or 40 mm. In various embodiments, the anchor can be characterized by the radial force being about 0.3 N or less at a diameter of 55 mm or less, e.g., at a diameter of 50 mm, 45 mm, or 40 mm. In various embodiments, the anchor can be characterized by the radial force being about 0.2 N or less at a diameter of 55 mm or less, e.g., at a diameter of 50 mm, 45 mm, or 40 mm.

The anchor can be characterized by a compressive elastic deformation diameter which can be expressed in absolute or relative terms. In various embodiments, the compressive elastic deformation diameter is about 12 mm or less, e.g., about 8 mm or less. In some cases, the compressive elastic deformation diameter is a percentage of the relaxed diameter of about 30% or less, e.g., about 20% or less.

At least one advantage resulting from anchoring at the duodenal bulb is that the pyloric orifice may be allowed to open and close normally. As described above, the length of the anchor is minimal to ensure that the ampulla of vater is not blocked or impeded. The distance in an average adult human between the pylorus and the ampulla of vater is at least about 2 inches. Thus, the length of the anchor is preferably less than about 2 inches (e.g., between 0.5 and 2 inches, e.g., about 0.5 inches, about 0.6 inches, about 0.7 inches, about 0.8 inches, about 0.9 inches, about 1 inch, about 1.1 inches, about 1.2 inches, about 1.3 inches, about 1.4 inches, about 1.5 inches, about 1.6 inches, about 1.7 inches, about 1.8 inches, about 1.9 inches, or about 2 inches).

Anchors can be configured with a drawstring for removal of the device according to methods described below. In particular, a drawstring connecting multiple proximal elements of the anchor (e.g., each proximal node of a wave anchor) can function to radially compress the proximal portion of the anchor upon being pulled in a proximal direction, e.g., by a hook-tipped catheter. Drawstring configurations are known in the art and described, for example, in U.S. Pat. Nos. 7,608,114, 8,137,301, 8,162,871, 9,155, 609, 7,476,256, 7,682,330, 7,981,163, 8,834,405, 9,237,944, 8,057,420, 8,771,219, and 9,095,416, each of which is incorporated herein by reference.

Sleeves

Gastrointestinal sleeves suitable for use as part of gastrointestinal implants are known in the art and described, e.g., in U.S. Pat. Nos. 7,025,791, 7,608,114, 7,695,446, 7,678,068, 7,122,058, 7,476,256, 7,815,589, 7,837,643, 8,057,420, 7,815,591, 7,771,382, and 7,766, 973, each of which is incorporated herein by reference.

In general, sleeves of the gastrointestinal implant are thin-walled, flexible, and floppy (i.e., they do not support the entirety of their weight, for example, if stood on end, they would buckle). Thus, sleeves can reduce or eliminate contact of chyme with walls of the intestine or digestive solutions secreted therefrom while transmitting natural peristaltic forces to propel the chyme through the intestines. After chyme from the stomach has passed through the sleeve, the sleeve may become thin and floppy, permitting the sleeve to contour to the inner walls of the intestine. In some cases, the sleeve is substantially non-compliant and drapes away from the intestinal walls, thereby permitting pancreatic juices to flow unimpeded into the duodenum through the ampulla of vater. Passage of chyme through the sleeve is also enhanced if the sleeve is made from a material having a low coefficient of friction (e.g., a static or kinetic coefficient of friction of less than about 0.3, e.g., about 0.29, about 0.28, about 0.27, about 0.26, about 0.25, about 0.24, about 0.23, about 0.22, about 0.21, about 0.2, about 0.19, about 0.18, about 0.17, about 0.16, about 0.15, about 0.14, about 0.13, about 0.12, about 0.11, or about 0.1, or less).

Such properties can be found in a sleeve formed from a fluoropolymer, such as expanded polytetrafluoroethylene (ePTFE), or from a combination with another material. For example, one such combination includes an ePTFE layer of material combined with a different fluoropolymer layer, such as fluorinated ethylene-propylene (FEP). The combination of the FEP with ePTFE provides a low coefficient of friction while also being substantially non-permeable or slightly permeable. In some embodiments, another material such as PTFE is applied to an ePTFE substrate using vapor deposition. Alternatively or in addition, the sleeve can be formed using polyolefin films, such as low density polyethylene (LDPE), high density polyethylene (HDPE), and polypropylene. Other materials suitable for use as part of a sleeve include cast polytetrafluoroethylene (e.g., TEFLON™), cast PTFE with FEP or perfluoroalkoxy (PFA) coating on a PTFE to minimize pin holes, extruded FEP and extruded PFA. These materials are solid and substantially non-porous in contrast to ePTFE, which is generally porous. These materials are also considered to be fluoropolymers. In some cases, the wall thickness of the sleeve is less than about 0.0025 inches (e.g., between 0.0003 and 0.0025 inches, e.g., from 0.0003 to 0.0010 inches, from 0.0010 to 0.0015 inches, from 0.0015 to 0.0020 inches, or from 0.0020 to 0.0025 inches, e.g., about 0.001 inches).

The length of the sleeve ranges from about one foot to about five feet (e.g., about 30 cm to about 150 cm). In some cases, the length of the sleeve is from 1 to 3 feet (e.g., 30 cm to 90 cm) from its proximal end (e.g., at flange) to its distal end (e.g., below the ligament of Treitz). In some embodiments, the sleeve has a length of 12 inches, 13 inches, 14 inches, 15 inches, 16 inches, 17 inches, 18 inches, 19 inches, 20 inches, 21 inches, 22 inches, 23 inches, 24 inches, 25 inches, 26 inches, 27 inches, 28 inches, 29 inches, 30 inches, 31 inches, 32 inches, 33 inches, 34 inches, 35 inches, or 36 inches, e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm. The length of the sleeve can be selected to bypass the duodenum and a portion of the jejunum. The length may be increased to further decrease absorption by bypassing a longer section of the jejunum. Thus, the length of the sleeve is variable and may be dependent on the patients height, weight, or body mass index.

The sleeve can have a diameter similar to that of a normal subject's intestine, e.g., at the duodenum or jejunum. Additionally or alternatively, the diameter (e.g., maximum diameter) of the sleeve can be from 0.5 to 3 inches (e.g., from 1.0 to 2.0 inches, e.g., about 1.5 inches). By maximum diameter is meant the diameter when the sleeve is open and has a substantially circular cross-section.

The proximal portion and distal portion may be substantially similar in material, wall-thickness, intrinsic diameter, and other physical properties. In other embodiments, the intrinsic diameter of the sleeve varies along its length.

In some cases, the invention provides eversion resistant sleeves. Eversion resistant sleeves refer to sleeves that resist proximal eversion (e.g., aberrant proximal movement through the anchor and/or pyloric orifice that may cause obstruction to the flow of chyme). Eversion resistant sleeves may be made from a thickening of the sleeve material, e.g., at a portion of the sleeve distal to the anchor, for example, as described in U.S. Pat. No. 7,766,973, which is herein incorporated by reference.

In some embodiments, markings can be added to the sleeve (e.g., at its exterior surface) to detect the position and orientation of the sleeve on a fluoroscopic image and whether the sleeve is twisted. For example, a stripe can be painted down the length of the device using tantalum impregnated ink, or tantalum bands can be bonded to the exterior surface of the device.

Delivery Systems

The present invention features delivery systems for placing a gastrointestinal implant in a patient's gastrointestinal tract. Delivery systems include a delivery catheter including, attached to its distal end, a container assembly for housing the gastrointestinal implant (e.g., all or a portion of the gastrointestinal implant) during delivery of the gastrointestinal implant in a patient. The gastrointestinal implant itself may be included in the delivery system or separate from the delivery system. For example, one embodiment of the delivery system may be compatible with various types of gastrointestinal implants (e.g., gastrointestinal implants having barbed anchors, unbarbed anchors, or transpyloric elements, such as a flange), as a modular system. In general, the container assembly includes a proximal capsule and a distal cap. The distal cap is configured, upon reaching a target position within a patient's gastrointestinal tract, to eject from (e.g., off of the outer perimeter of) the proximal capsule as part of the installation of the gastrointestinal implant. The distal cap can be completely ejected from the proximal capsule upon deployment (e.g., without being tethered by a catheter).

Delivery System Assembly

A delivery system of the present invention can be assembled by loading a gastrointestinal implant into a distal capsule and a proximal cap to form a container assembly. The methods of the invention also include preparation of a delivery system for placement of a gastrointestinal implant in a patient. In particular, methods of assembling a delivery system include inserting a proximal portion of a gastrointestinal implant (e.g., an anchor) within a proximal capsule (e.g., a proximal capsule connected to a delivery catheter) and inserting a distal portion of the gastrointestinal implant (e.g., an elongate distal portion, e.g., a sleeve) within a distal cap. The distal cap is attached to the proximal capsule (e.g., before, during, or after loading of the gastrointestinal implant), and the resulting device is referred to as the container assembly.

Figure 3:
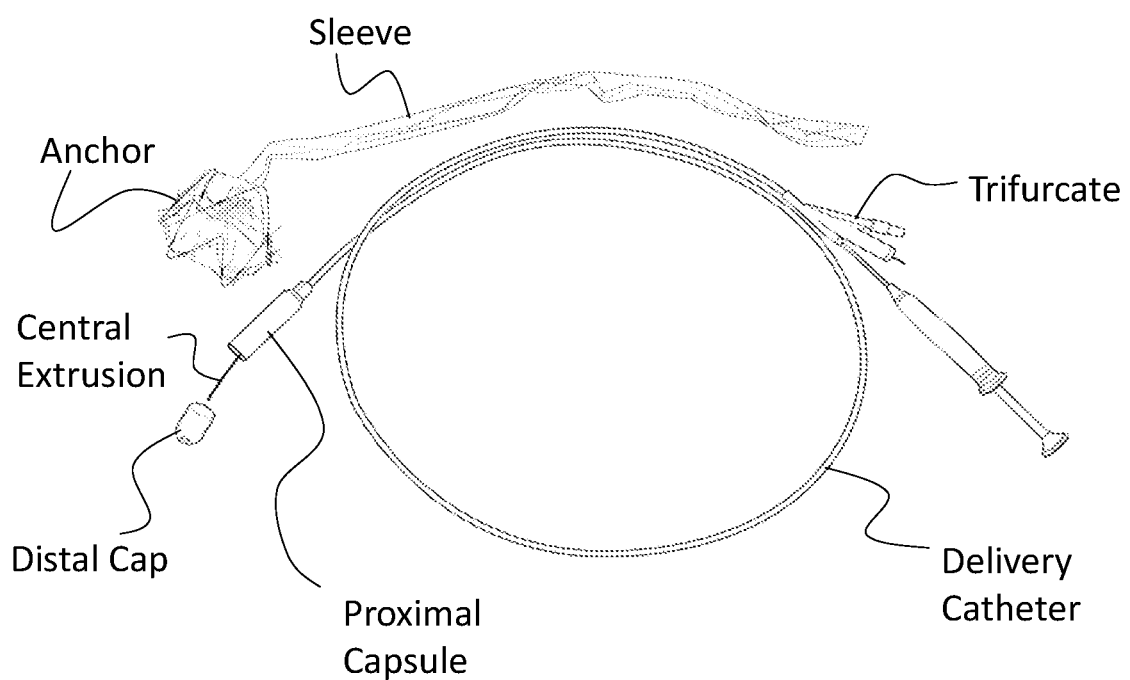
FIG. 3 is a photograph of a disassembled delivery system of the invention, showing gastrointestinal implant having a distal sleeve and a proximal anchor, and a delivery catheter connected to a proximal capsule attachable to a distal cap. A central extrusion runs through a lumen of the delivery catheter.
Figure 4:
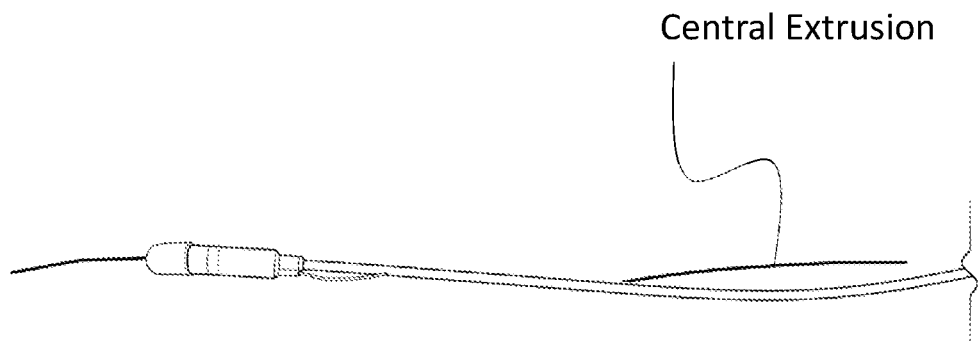
FIG. 4 is a photograph of an alternative embodiment of a delivery system, in which the central extrusion is external to the delivery catheter at the region proximal to the proximal capsule.

FIG. 3 shows an embodiment of a disassembled delivery system. The delivery catheter has a proximal capsule at its distal end, which is configured to house a proximal portion of a gastrointestinal implant (e.g., a proximal anchor) during delivery of the gastrointestinal implant into a patient. In some embodiments, the delivery system includes a central extrusion (e.g., a tube comprising a lumen) that runs through and extends from the lumen of the proximal capsule. The central extrusion can be configured to contain a guidewire for directing the delivery system through the gastrointestinal tract. In some cases, the central extrusion runs through the delivery catheter, as shown in FIG. 3. Alternatively, the central extrusion can run through the proximal capsule, but exit the proximal end of the proximal capsule and run along the exterior of all or part of the delivery catheter, as shown in FIG. 4.

Figure 5:
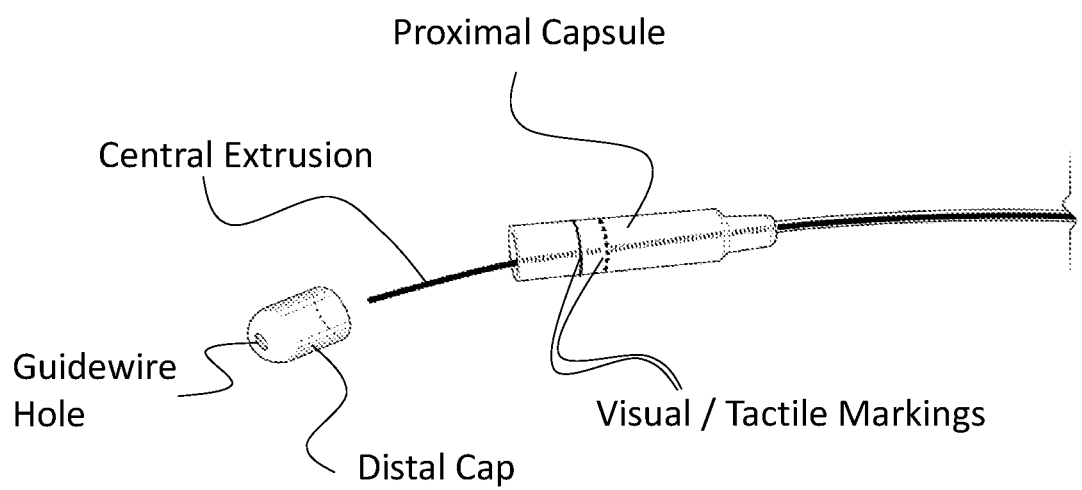
FIG. 5 is a photographic close-up view of a disassembled container assembly, showing the detail of the distal cap, which has a guidewire hole through which the central extrusion and guidewire is configured to pass.

The delivery system also includes a distal cap, which can be configured to fit onto the distal end of the proximal capsule. To accommodate passage of the central extrusion and/or guidewire, the central cap can have a guidewire hole (e.g., centrally, along its longitudinal axis). A close-up view of the distal cap and proximal capsule in one embodiment of the delivery system is shown in FIG. 5.

To load the gastrointestinal implant into the proximal capsule, the gastrointestinal implant is positioned longitudinally in alignment with the proximal capsule and/or delivery catheter such that the proximal end of the gastrointestinal implant abuts the distal end of the proximal capsule. The gastrointestinal implant is then loaded into the lumen of the proximal capsule, starting from its proximal end and proceeding to its distal end. In some cases, the relaxed diameter or width of the proximal end of the gastrointestinal implant (e.g., the anchor, e.g., a wave anchor) will exceed the diameter or corresponding width of the proximal capsule lumen, in which case all or part of the proximal portion of the gastrointestinal implant can be radially collapsed (e.g., manually or automatically) to fit within the proximal capsule. For example, an anchor (e.g., a wave anchor) is radially expandable and can be radially compressed to fit into the proximal capsule. In the case of transpyloric anchor systems, an element proximal to an anchor (e.g., a planar proximal element, such as a ring or a hoop) can be deformed (e.g., compressed in the longitudinal direction) for insertion into the proximal capsule. In the case of flanged gastrointestinal implants, the flange proximal to the anchor can be compressed and inserted into the proximal capsule prior to loading of the anchor, such that the flange, anchor, and/or all or a portion of the sleeve are arranged longitudinally within the proximal capsule in a proximal-to-distal alignment. Optionally, the anchor can be fully loaded within the proximal capsule, such that no portion of the anchor extends beyond the distal opening of the proximal capsule. In this case, the distal end of the anchor can be positioned 1 mm to 20 mm from the distal opening of the proximal capsule (e.g., from 1 mm to 5 mm, from 5 mm to 10 mm, from 10 mm to 15 mm, or from 15 mm to 20 mm from the distal opening of the proximal capsule).

After loading a proximal region of the gastrointestinal implant (e.g., an anchor and any transpyloric elements proximal thereto), all or a portion of the distal region of the gastrointestinal implant (e.g., the sleeve) can be loaded into the proximal capsule. In many cases, loading of the anchor will inherently require loading a portion of the sleeve, since the anchor may be directly connected to the sleeve. For example, a wave anchor may be matched in undulating shape by an undulating proximal end of the sleeve. In this case, some proximal portions of the sleeve are proximal to distal regions of the anchor and therefore must be within the lumen of the proximal capsule when the anchor is fully loaded. Additionally or alternatively, a distal portion of gastrointestinal implant (e.g., sleeve) can be manually loaded into the proximal capsule.

In some cases, proximal capsule houses less than 10% of the length of the distal portion of the gastrointestinal implant (e.g., sleeve, e.g., less than 9%, less than 8%, less than 7%, less than 6%, less than 5%, less than 4%, less than 3%, less than 2%, or less than 1%, e.g., from 8% to 10%, from 6% to 8%, from 4% to 6%, from 2% to 4%, or from 0% to 2% of the length of the sleeve). The portion of the sleeve housed within the proximal capsule can be the proximal portion of the sleeve (e.g., a portion that is attached to the anchor).

Figure 6:
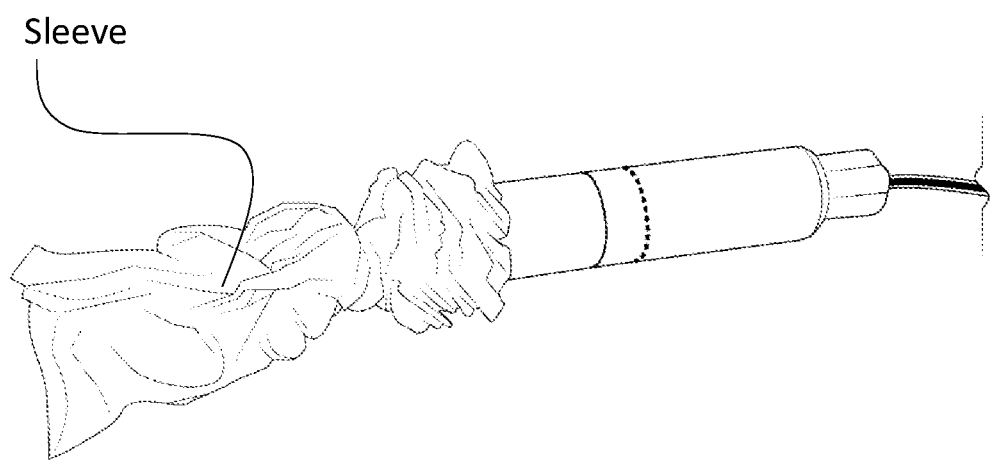
FIG. 6 is a photograph of a partially assembled container assembly. The anchor is positioned within the lumen of the proximal capsule, and the sleeve has been bunched up around the central extrusion.
Figure 10:
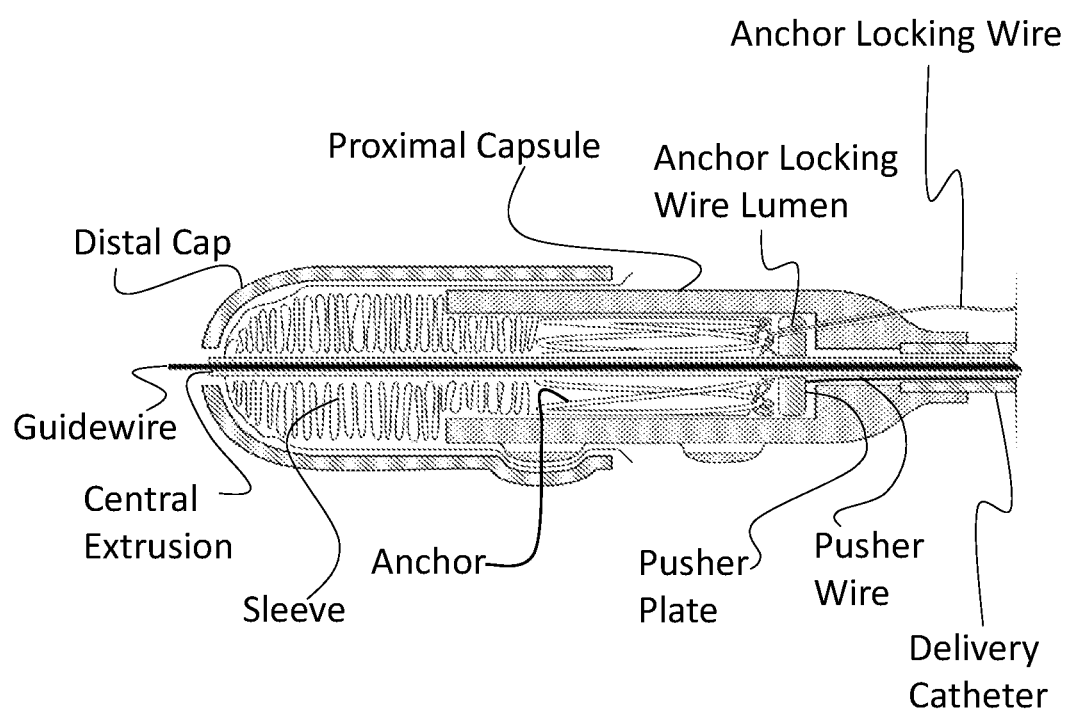
FIG. 10 is a cross-sectional view of one embodiment of the container assembly in which a central extrusion runs centrally along its longitudinal axis to accommodate passage of a guidewire.
Figure 11:
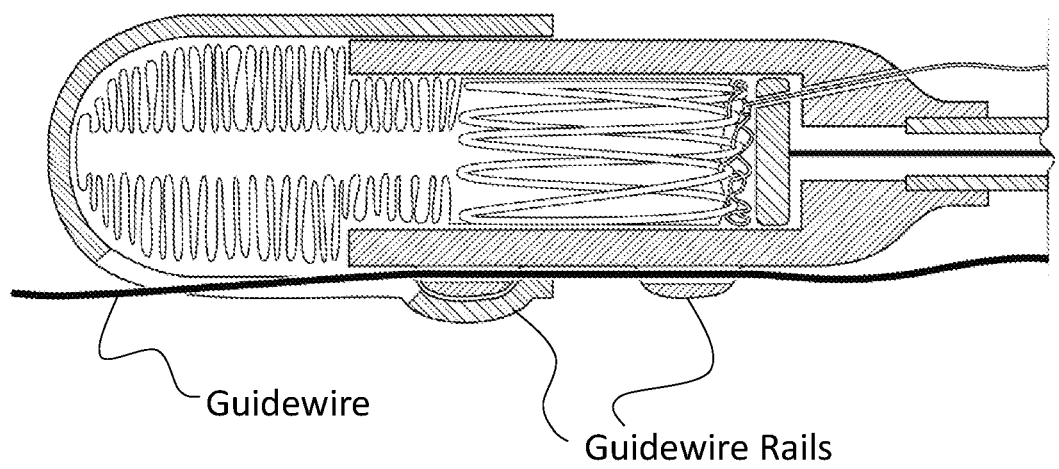
FIG. 11 is a cross-sectional view of an alternative embodiment of the container assembly in which no central extrusion is present. In this embodiment, the guidewire runs along the exterior of the container assembly, through two guidewire rails.

To prepare the remaining portion of the gastrointestinal implant (e.g., the remaining portion of the sleeve, e.g., the region of the sleeve extending distally from the proximal capsule), the remaining portion can be "bunched up" (i.e., radially and longitudinally constrained, thereby creating radial undulations, represented by FIGS. 10 and 11) around the longitudinal axis, as shown in FIG. 6. The longitudinal axis may have a central extrusion around which the distal region of the gastrointestinal implant can be positioned, or there may be no central extrusion at the longitudinal axis.

Figure 7:
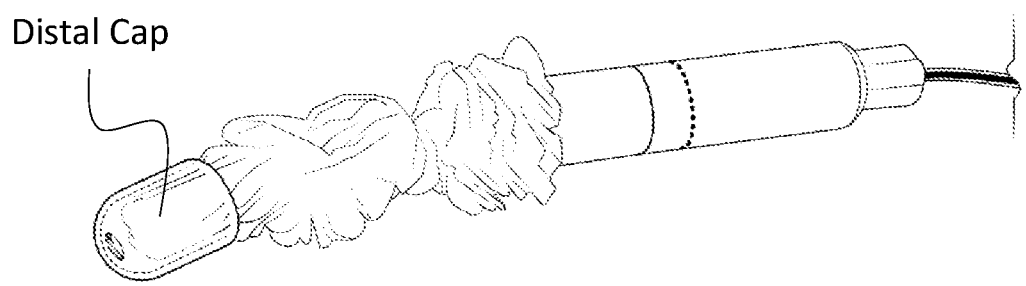
FIG. 7 is a photograph of a partially assembled container assembly in which the distal cap has been positioned for packing of the sleeve therewithin. The distal cap is partially within the distal portion of the sleeve.

Once all or a portion of the remaining distal portion of the gastrointestinal implant (e.g., a distal portion of the sleeve) is constrained toward the proximal capsule, a distal cap may be positioned at or near the distal end of the gastrointestinal implant. Alternatively, the distal cap may be used to assist in constraining the distal portion of the gastrointestinal implant (e.g., sleeve). In one embodiment, the proximal portion of the distal cap is positioned within the distal opening of the sleeve, as shown in FIG. 7. The sleeve can overlap the distal cap, for example, by from 0.01 to 1 inch (e.g., from 0.01 to 0.1 inch, form 0.1 to 0.2 inches, from 0.2 to 0.5 inches, or from 0.5 to 1 inches longitudinally). In some cases, the sleeve overlaps the distal cap by about a quarter inch.

Figure 8:
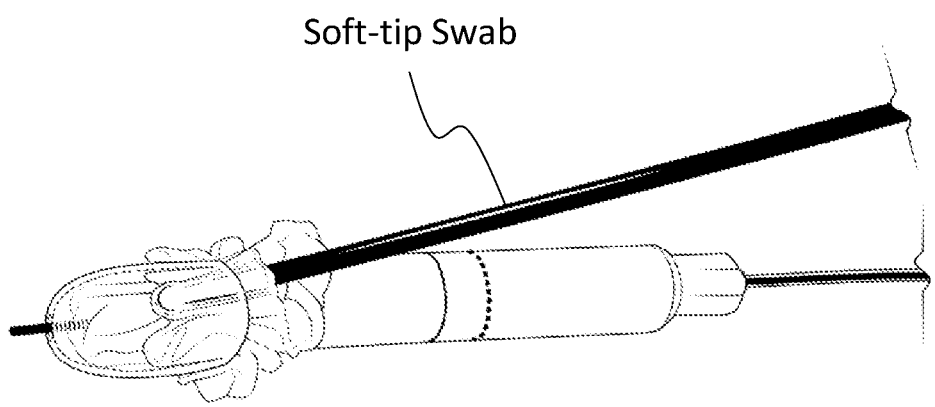
FIG. 8 is a photograph showing the sleeve being packed into the distal cap with a soft-tip swab. At this point, the distal cap is not attached to the proximal capsule.

At this stage in the assembly process, the distal portion of the gastrointestinal implant can be packed into the distal cap, for example, by using a tool to distally push the constrained region of the sleeve into the distal cap, as shown in FIG. 8. Any suitable method of loading can be utilized. It will be appreciated by a person of skill in the art that it may be favorable that the sleeve be loaded into the distal cap such that the intrinsic proximal-to-distal orientation of the sleeve is substantially preserved in order to facilitate elongation and expansion upon deployment from the container assembly (e.g., to prevent tangling and/or twisting). Alternatively, the sleeve may be everted to promote correct orientation upon elongation. For example, the distal movement of the distal cap through the gastrointestinal tract may revert the sleeve to the correct configuration as it elongates.

All or a portion of (e.g., a majority of) the distal portion of the gastrointestinal implant (e.g., sleeve) can be loaded into the distal cap. For example, 10% to 100% of the length or surface area of the sleeve can be loaded into the distal cap (e.g., from 10% to 20%, from 20% to 30%, from 30% to 40%, from 40% to 50%, from 50% to 60%, from 60% to 70%, from 70% to 80%, from 80% to 85%, from 85% to 86%, from 86% to 87%, from 87% to 88%, from 88% to 89%, from 89% to 90%, from 90% to 91%, from 91% to 92%, from 92% to 93%, from 93% to 94%, from 94% to 95%, from 95% to 96%, from 96% to 97%, from 97% to 98%, from 98% to 99% or from 99% to 100% of the length or surface area of the sleeve).

Figure 9:
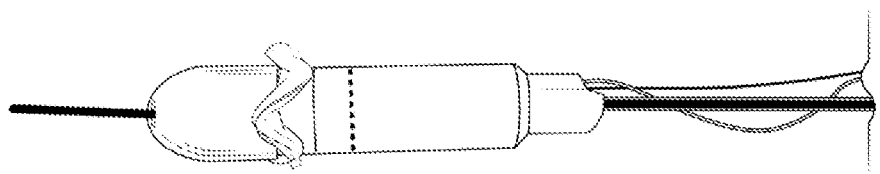
FIG. 9 is a photograph of the assembled container assembly, in which the distal cap is attached to the proximal capsule. The distal-most segment of the sleeve can be seen exposed from beneath the distal cap.

The cap can be attached to the proximal capsule (e.g., by an interference fit) before or after loading of the distal portion of the gastrointestinal implant, or at any point during loading. In some cases in which the distal end of the sleeve overlaps the proximal end of the distal cap, upon completion of loading into the cap, the overlapping portion of the sleeve remains outside the proximal container and the distal cap, as shown in FIG. 9.

In some cases in which a central extrusion is present, after the distal cap is attached to the proximal capsule, the central extrusion may be cut such that it does not substantially extend beyond the distal end of the distal cap. This can reduce the likelihood of becoming "snagged" during delivery to the target site in the gastrointestinal tract.

Delivery System Components and Mechanisms

The delivery system assembly includes the container assembly connected, at a proximal region (e.g., at its proximal end or a proximal region within the interior of the proximal capsule) to a delivery catheter. Delivery catheters include one or more lumens and are described in detail in U.S. Pat. No. 7,837,643, incorporated herein by reference in its entirety. Container assemblies of the present invention are configured to house a gastrointestinal implant for delivery to a region of the gastrointestinal tract, e.g., by ejecting the gastrointestinal implant while attached to the distal cap (e.g., such that the gastrointestinal implant and the distal cap are untethered from the proximal capsule). The container assembly is sized and shaped to house the gastrointestinal implant (e.g., a radially constrained gastrointestinal implant) while being suitable for delivery through a patient's mouth and gastrointestinal system (e.g., up to the duodenum). Thus, in some cases, the container assembly is less than 30 mm in width at one or more directions perpendicular to the longitudinal axis (e.g., diameter; e.g., less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, less than 10 mm, less than 9 mm, less than 8 mm, less than 7 mm, less than 6 mm, or less than 5 mm; e.g., from 5 mm to 30 mm, from 8 mm to 25 mm, from 10 mm to 20 mm, or from 12 mm to 15 mm in width at one or more directions perpendicular to the longitudinal axis (e.g., diameter)).

A cross sectional view of a loaded container assembly having a central extrusion is shown in FIG. 10, and a loaded container assembly not having a central extrusion is shown in FIG. 11. In each of these embodiments, the ejection mechanism (e.g., plunger) is illustrated. In these embodiments, the ejection mechanism includes a pusher plate and a pusher wire. The pusher plate has a distally-oriented surface configured to exert a distal force on the gastrointestinal implant (e.g., a proximal end of the gastrointestinal implant, e.g., a proximal end of an anchor) to deploy the device. Alternatively, the ejection mechanism can include a distal element other than a plate, such as a ring, or a non-circular element having suitable geometry and mechanical properties to displace the gastrointestinal implant.

The distal region of the ejection mechanism (e.g., pusher plate) can be articulated by a practitioner through a rigid pusher wire attached thereto. The pusher wire can run longitudinally through a lumen of the delivery catheter to a proximal region (e.g., a proximal end) of the delivery catheter. Optionally, the ejection mechanism includes a mechanism to prevent a practitioner from directing the pusher plate distally to such an extent that the pusher plate emerges from the distal end of the proximal capsule. Such mechanisms involve a moving stop and a static stop displaced proximally to the pusher plate, and are described in detail in U.S. Pat. No. 7,837,643, incorporated herein by reference in its entirety.

In some embodiments, the pusher plate is made of molded acrylonitrile butadiene styrene (ABS) plastic. In some embodiments, the pusher wire is made of nitinol.

Also shown in FIGS. 10 and 11 is a locking wire configured to prevent premature displacement of the pusher plate (e.g., plunger activation). The locking wire can be removably connected to (e.g., directly or indirectly, e.g., through an intermediate element) any region of the gastrointestinal implant. In some cases, the locking wire is removably connected to a proximal portion (e.g., a proximal end) of the gastrointestinal implant (e.g., at the anchor, e.g., at the proximal end of the anchor, e.g., at one or more proximal regions of the undulations of a wave anchor). In some cases, as shown in FIGS. 10 and 11, the locking wire can form a loop, or lasso-shape, and reversibly connect to the anchor around its proximal circumference. Additionally or alternatively, the locking wire can connect to, or be integrally part of, a suture or drawstring, e.g., connected to the proximal circumference of the anchor (e.g., a removal drawstring). The locking wire can run through a lumen within the delivery catheter to a proximal region of the delivery system.

Figure 12:
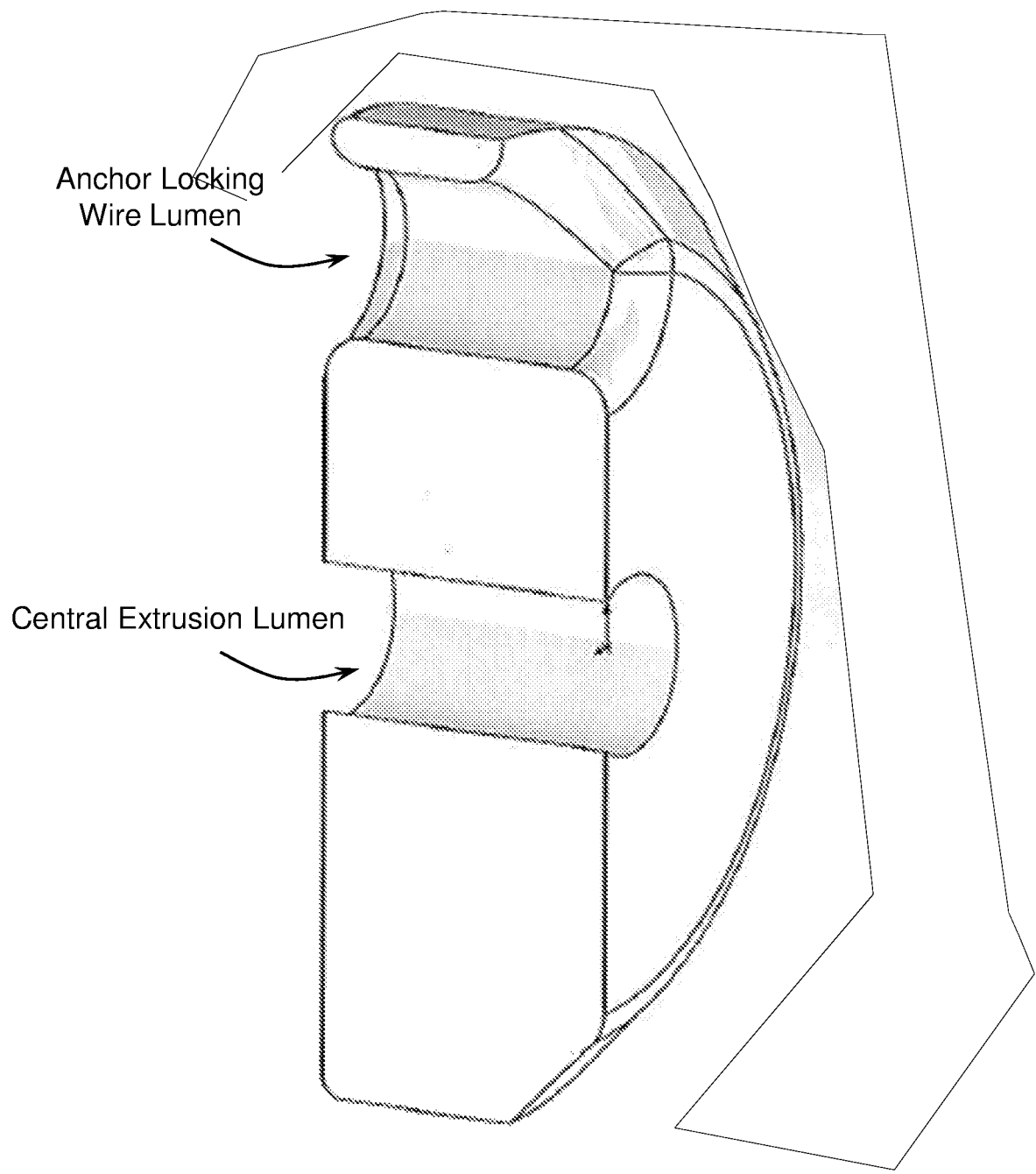
FIG. 12 is a drawing of a cross-section of a pusher plate having a central extrusion lumen and an anchor locking wire lumen.

The pusher plate can be configured to allow passage of the locking wire therethrough, e.g., by inclusion of a hole or lumen. FIG. 12 shows a drawing of a pusher plate having a locking wire lumen offset from a central extrusion lumen. In embodiments not including a central extrusion, such as shown in FIG. 11, the locking wire lumen may be at the center of the pusher plate. Alternatively, the locking wire may pass around the outer edge of the pusher plate, e.g., through a lumen within the proximal capsule, or between the outer edge of the ejection mechanism and the inner lumen of the proximal capsule.

Figure 14:
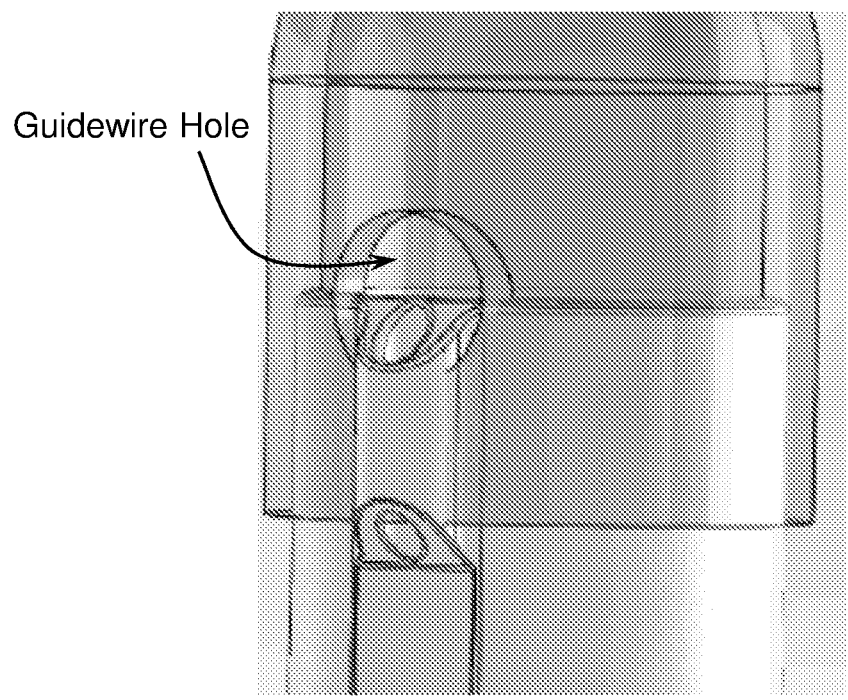
FIG. 14 is a drawing of a close-up view of the distal guidewire rail, showing the guidewire hole in the distal cap.

FIG. 14 demonstrates the method for removal of the locking wire. The suture of the wave anchor is pulled through a lumen that communicates from the inside of the capsule (where it is connected to the wave anchor) to the proximal end of the capsule. By withdrawing the locking wire, the sutures and thus allows the wave anchor and liner to be ejected from the capsule.

In some embodiments, the locking wire is made of stainless material and coated with PTFE.

FIG. 12 further shows the central extrusion lumen, which may or may not be present, depending on the configuration of the guidewire relative to the delivery system. For example, FIG. 10 shows an embodiment of the delivery system wherein the guidewire passes through the central extrusion, whereas FIG. 11 shows an embodiment of the delivery system wherein the guidewire passes through two guidewire rails on the periphery of the proximal capsule. A delivery device may be compatible with both configurations by incorporating a central extrusion in addition to one or more guidewire rails, as shown in FIG. 10.

Figure 13:
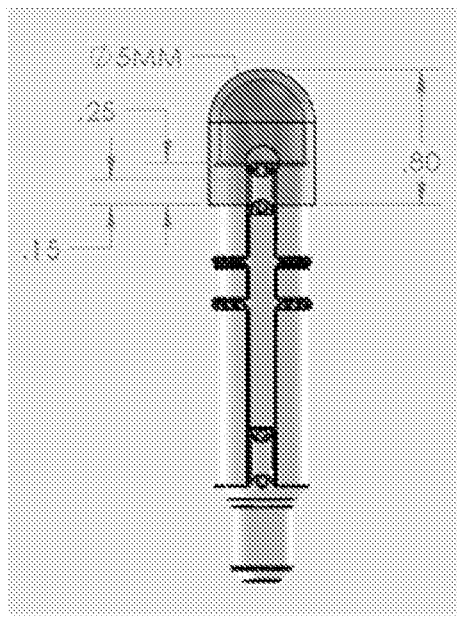
FIG. 13 is a drawing of a container assembly not including a central extrusion. The distal cap has a guidewire hole positioned at the distal opening of the distal guidewire rail through which the guidewire is configured to pass.

Each of these configurations imposes particular design requirements on the delivery device. In particular, the distal cap can include a hole or lumen through which the guidewire passes. Delivery systems including a central extrusion can feature a distal cap that has a hole through its longitudinal axis (i.e., at or near its center), sized to match or slightly exceed the outer diameter of the central extrusion. The edges of the hole may be chamfered or rounded. In embodiments featuring peripheral guidewire passage (e.g., through one or more guidewire rails), the distal cap can include a guidewire hole on its periphery. The guidewire hole can be configured to match (e.g., concentrically overlay) the distal-most opening of the guidewire rail. Such a configuration is shown in FIGS. 13 and 14. In some cases, the proximal capsule is compatible for guidewire passage through both a central extrusion and peripheral rails. In this case, the proximal capsule can be compatible with various types of distal caps (e.g., distal caps with central guidewire holes and distal caps with peripheral guidewire holes).

In general, the distal cap is atraumatic, e.g., in shape, size, material, and/or texture. For example, in some cases, the distal cap is made of a soft material (e.g., a material comprising silicone). The material of the cap (e.g., a silicone cap) can have a shore 00 hardness from 0 to 100 (e.g., from 10 to 90, from 20 to 80, from 30 to 70, or from 40 to 60; e.g., from 0 to 10, from 10 to 20, from 20 to 30, from 30 to 40, from 50 to 60, from 60 to 70, from 70 to 80, from 80 to 90, or from 90-100). In some cases, the distal cap comprises silicone and has a shore 00 hardness of between 10 and 100, e.g., about 50 (e.g., 50 durometer silicone). In some cases, the distal cap is rounded (e.g., for atraumatic delivery). For example, the distal end of the distal cap can be substantially hemispherical in shape. Alternatively, the distal end of the distal cap can have a "bullet" shape.

The distal cap can be removably connected or attachable to the proximal capsule by any suitable means (e.g., an interference fit, e.g., a snap fit). In some cases, the distal cap is connected or attachable to the proximal capsule by an interference fit (e.g., the inner diameter of the proximal portion of the distal cap can be slightly less than the outer diameter of the distal region of the proximal capsule), such that, upon actuation of the ejection mechanism, the distal cap disengages the proximal capsule to allow release of the gastrointestinal implant from the proximal capsule. In particular, the inner diameter of the proximal end of the distal cap (e.g., a silicone distal cap, e.g., a 50 durometer silicone distal cap) can be between 20% and 100% of the outer diameter of the distal end of the proximal capsule (e.g., between 30% and 99%, between 40% and 98%, between 50% and 97%, between 60% and 96%, between 50% and 95%, between 60% and 94%, between 70% and 93%, between 80% and 92%, or between 85% and 90% of the outer diameter of the distal end of the proximal capsule). The relative inner and outer diameters of the distal cap and proximal capsule, respectively, will depend, e.g., on the material properties and wall thickness of the distal cap, as well as the required ejection force.

Figure 15:
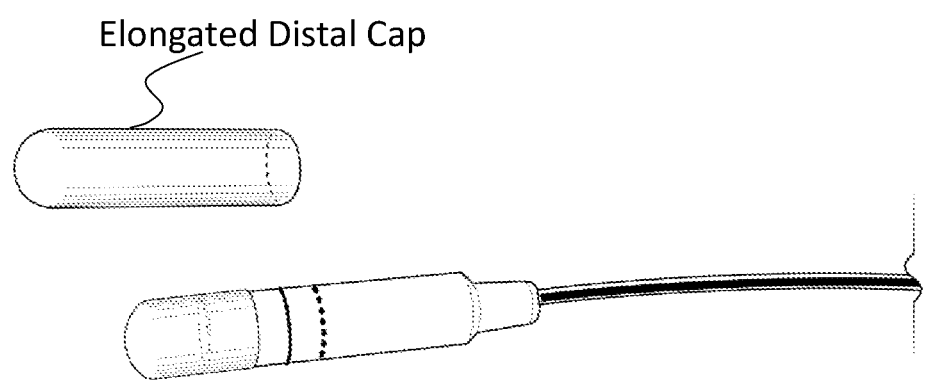
FIG. 15 is a photograph showing a capsule assembly fitted with a distal cap. Also shown is a longer version of the distal cap configured to house a larger gastrointestinal implant.

The distal cap generally has dimensions suitable for housing all or a portion of the distal portion of the gastrointestinal implant (e.g., all or a portion of (e.g., a majority of) a sleeve), while having a sufficiently small radius to pass through the gastrointestinal system. In some cases, the distal cap has a length from 10 mm to 100 mm (e.g., from 11 mm to 90 mm, from 12 mm to 80 mm, from 13 mm to 70 mm, from 14 mm to 60 mm, from 15 mm to 50 mm, from 16 mm to 40 mm, from 17 mm to 30 mm, or from 18 mm to 25 mm, e.g., about 20 mm). An alternative embodiment of a distal cap having an increased length is shown in FIG. 15. The distal cap can be hollow or semi-hollow, having one or more walls from 1 mm to 5 mm in thickness (e.g., from 1 mm to 1.5 mm, from 1.5 mm to 2.0 mm, from 2.0 mm to 2.5 mm, from 2.5 mm to 3.0 mm, from 3.0 mm to 3.5 mm, from 3.5 mm to 4.0 mm, from 4.0 mm to 4.5 mm, or from 4.5 mm to 5.0 mm).

Any one or more components of the delivery system can include visual, radiographic, or tactile markings. In some cases, the proximal capsule features one or more visual markings, e.g., for visualization by a practitioner by endoscope. Markings can include one or more (e.g., 1, 2, 3, 4, or more) circumferential lines around the proximal capsule at a length informative of the anatomic position of the capsule, e.g., relative to the pyloric sphincter. In embodiments having multiple markings (e.g., circumferential lines), the markings may be a different color, pattern, texture, or have any other differentiating characteristic helpful to the practitioner to decipher its location as it moves through the gastrointestinal tract. The marking may additionally or alternatively provide tactile feedback to the practitioner, e.g., by featuring ridges to exert discrete points of resistance to longitudinal movement at particular locations of interest. For example, the markings (e.g., visual or tactile markings), when sensed by the practitioner, may indicate that the delivery system is positioned accurately for deployment (e.g., that the capsule is within the pyloric sphincter and the distal cap is at the duodenal bulb). Additional details regarding markings and uses thereof are found in U.S. Pat. No. 7,837,643, incorporated herein by reference in its entirety.

Any one or more components of the delivery system can be made of suitable materials known in the art.

Methods of Deliver and Methods of Treatment

The invention further provides methods for delivering gastrointestinal implants, such as those described above, using delivery systems described above. Further provided are methods for treatment of metabolic disorders, such as type 2 diabetes, non-alcoholic steatohepatitis (NASH), non-alcoholic fatty liver disease (NAFLD), obesity, and related comorbidities thereof.

Methods of Delivery

Featured herein are methods of positioning a gastrointestinal implant using any of the delivery systems described above or prepared or assembled by methods described above. In particular, the methods include directing the container assembly into a patient's gastrointestinal tract, securing an anchor of the gastrointestinal implant (e.g., a proximal anchor) to a luminal wall of the gastrointestinal tract (e.g., a luminal wall of the duodenum, e.g., a luminal wall of the duodenal bulb), and allowing peristalsis and/or distal passage of fluid (e.g., peristalsis-induced flow of chyme or other endogenous fluids, or exogenous addition of fluid or other material) to extend the elongate distal portion (e.g., during and/or after removal of the delivery system from the patient's gastrointestinal tract). Thus, the methods of the present invention obviate the need for distal extension of a catheter (e.g., an inner catheter, or an inner shaft) to manually extend the distal end of the gastrointestinal implant (e.g., the distal end of an elongate portion, e.g., a sleeve), potentially resulting in shorter operation times and fewer adverse effects.

In some cases, the gastrointestinal implant is delivered to the duodenal bulb. For purposes of anchoring a gastrointestinal implant, the duodenal bulb offers several advantages over other areas in of gastrointestinal tract. First, the duodenal bulb is proportionally sized to capture an anchor. That is, it provides a cavity having a relatively large diameter bounded by anatomies having smaller diameters in both the proximal and distal directions. Thus, the duodenal bulb is naturally configured to retain a suitably shaped anchor. Additionally, the duodenal bulb is relatively less active than either the pylorus or the distal portions of the duodenum. Movement of the surrounding tissue can act to dislodge an anchor over time. The duodenal bulb, at least in part, acts as a holding area for chyme received from the stomach. Thus, the duodenal bulb provides a more stable anchoring platform as there is relatively less movement than at other portions of the gastrointestinal tract.

A proximal portion of the small intestine (e.g., the duodenum) can be expanded in order to create a working space for the practitioner. One method of expanding a proximal portion of the small intestine is to direct a fluid into the duodenum via a working channel in the gastro-scope. Examples of suitable fluids include gases (e.g., air, nitrogen, and/or carbon dioxide) or liquids (e.g., water and/or saline). In some embodiments, the fluid is a liquid mixture of saline and a contrast medium. Examples of suitable contrast mediums include a fluorescent material, a radiopaque material, or a contrast medium commonly used for intravenous urography (e.g., preparations of diatrizoate sodium and diatrizoate meglumine). The liquid can be a mixture of about 75% saline and about 25% RENOGRAFIN™ (available from Bracco Diagnostics, Inc. Corporation, East Princeton, N.J.).

The exact amount of fluid needed to sufficiently expand the duodenum will depend on variables such as the size of the patient's gastrointestinal tract, the preferences of the practitioner, and/or the length of the gastrointestinal implant to be delivered. In some embodiments, at least 60 milliliters of a fluid are used to expand the duodenum. In further embodiments, at least 200 milliliters of a fluid are used to expand the duodenum. 200 milliliters of a fluid would be useful for delivering, for example, a gastrointestinal sleeve that is about two feet in length. In further embodiments, at least 500 milliliters of a fluid are used to expand the duodenum. In still further embodiments, about 600 milliliters of a fluid are used to expand the duodenum which would be useful for delivering, for example, a gastrointestinal sleeve that is about 4 feet in length.

After the small intestine has been expanded to the desired extent, a length of guidewire is directed through the working channel of a gastro-scope and into the delivery site (e.g., the proximal portion of the duodenum). An example of a suitable guidewire is about a 13-foot length of super-stiff 0.035 inch guidewire. Other suitable guidewires are known in the art. Once a sufficient length of guidewire is in the desired location, the gastro-scope can be removed.

Figure 16:
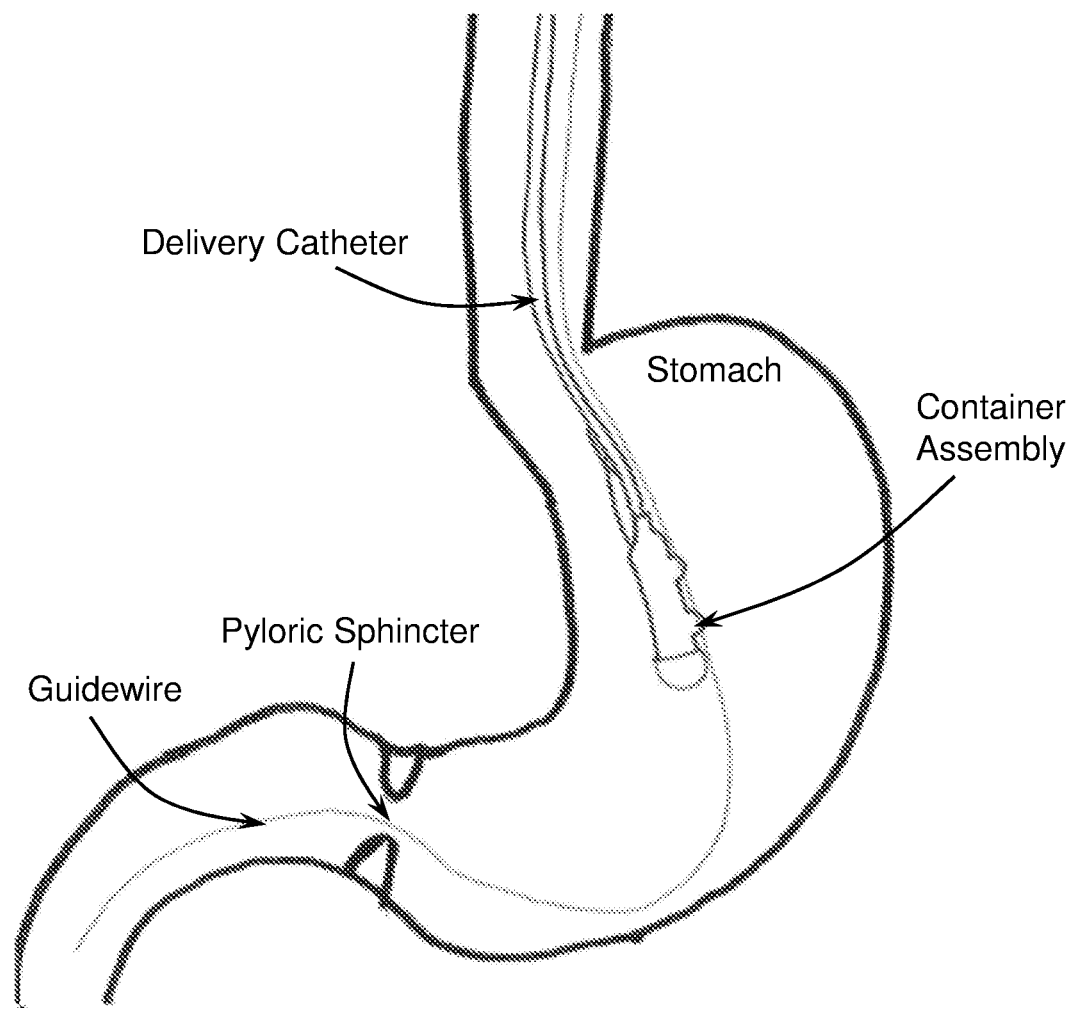
FIG. 16 is a drawing of a delivery system being directed through a gastrointestinal tract using a guidewire.
Figure 17:
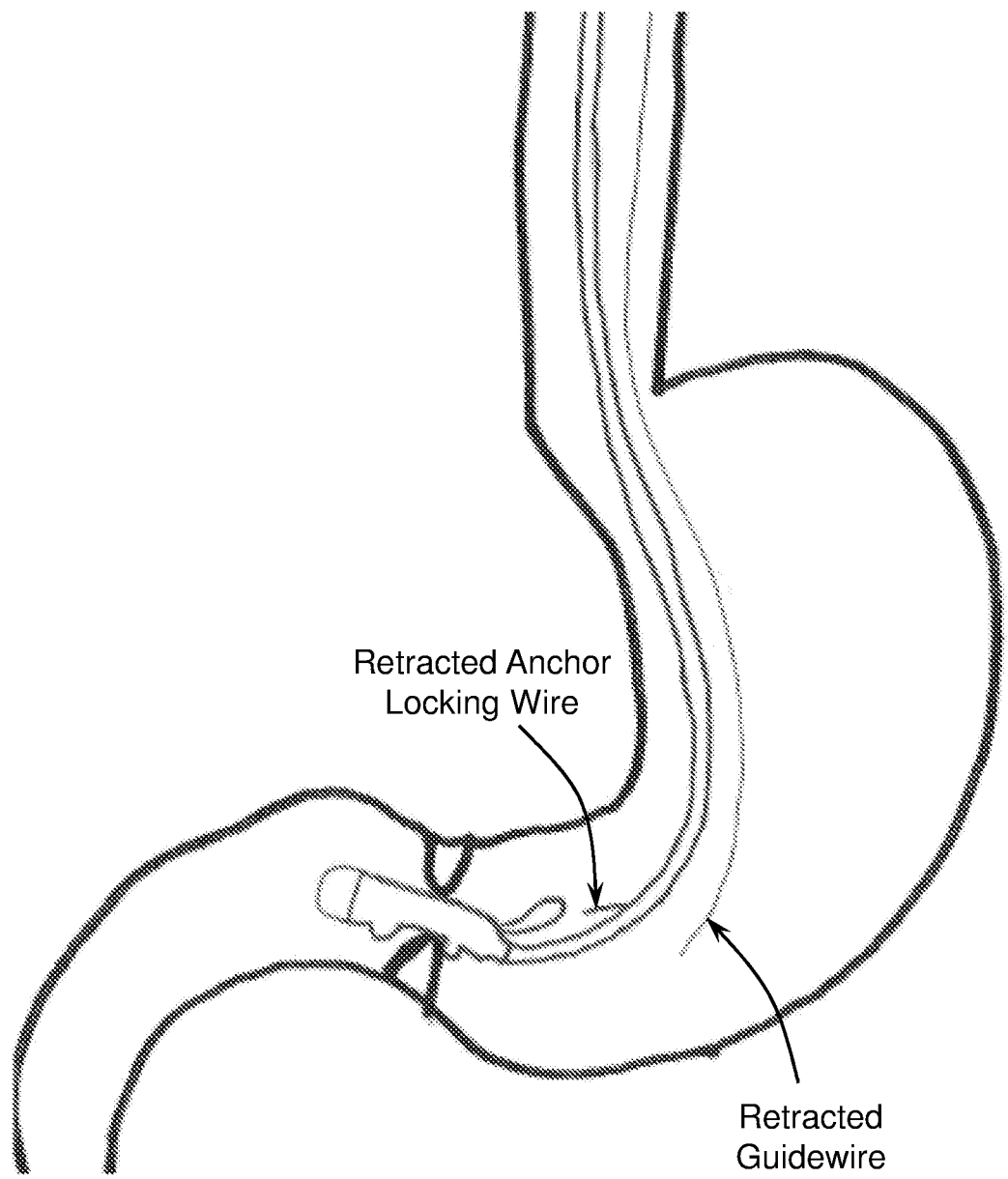
FIG. 17 is a drawing showing the proximal capsule positioned for deployment of the gastrointestinal implant. The proximal capsule is traversing the pyloric sphincter, and the distal cap is distal to the pyloric sphincter, in the duodenal bulb. In this drawing, the guidewire is being retracted, and the anchor locking wire has been retracted to unlock the ejection mechanism.

Once the guidewire is in the desired location and the gastro-scope has been removed, the delivery system can be directed into the duodenum. The leading or distal end of the catheter can be attached, assembled to, or include a capsule assembly defining a guidewire lumen along its side or through its central longitudinal axis, as described above. The guidewire can be directed through the guidewire lumen, and the capsule assembly can be advanced or directed along the guidewire, as shown in FIG. 16. In some embodiments, the distal portion capsule assembly (e.g., a portion including the distal cap) is positioned at a point distal to the pylorus (e.g., within the duodenal bulb), as shown in FIG. 17. At this point, the practitioner can utilize markers on the proximal capsule (e.g., visual and/or tactile markers, as described above) to find the precise position desired. Once the capsules assembly is at the desired location in the duodenum, the guidewire can be removed from the gastrointestinal tract. In some cases, the anchor locking mechanism is disengaged (e.g., by retracting a luer connected thereto at the proximal end of the delivery catheter), freeing the ejection mechanism for actuation. The proximal end of the capsule can have at least two tapers. The gastrointestinal implant device can be positioned using the tapers. The distal taper can be used for alignment with the entrance to the pylorus for placement of the anchor in an intermediate position within the duodenal bulb.

The gastrointestinal implant can be deployed using an ejection mechanism described above. For example, a practitioner can distally push a proximal end of a pusher wire from the proximal end of the delivery catheter, to distally push a plunger within the proximal capsule against the gastrointestinal implant. The plunger exerts a force on the gastrointestinal implant, which is transmitted through all or a portion of the gastrointestinal implant to the distal cap, which thereby detaches from the proximal capsule. The practitioner can continue to apply force to the plunger to completely eject the gastrointestinal implant. In some embodiments, the plunger is pushed from 1 to 2 inches to completely deploy the gastrointestinal implant. In some cases, the plunger exerts a force directly to the anchor. In other cases, the plunger exerts a force directly to a component of the gastrointestinal implant that is proximal to the anchor (e.g., a transpyloric element, e.g., a flange). For example, in a transpyloric device, the plunger may directly contact and exert a force on a proximal element, which can thereby transmit that force through another one or more portion of the gastrointestinal implant (e.g., the anchor and/or the sleeve) to force the distal cap to detach from the proximal capsule.

Figure 18:
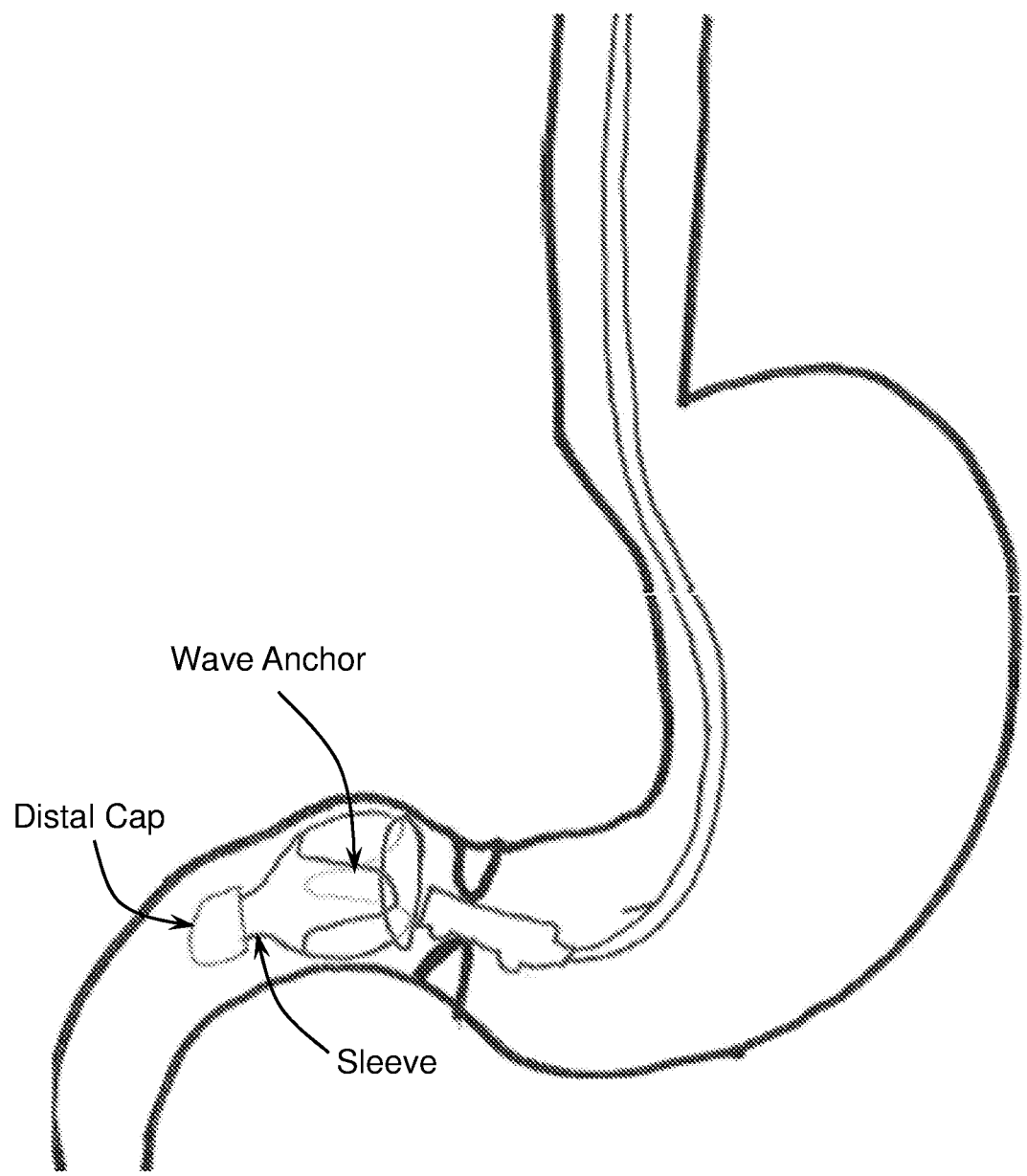
FIG. 18 is a drawing showing the deployed gastrointestinal implant in the duodenal bulb. The gastrointestinal implant is attached to the distal cap.
Figure 19:
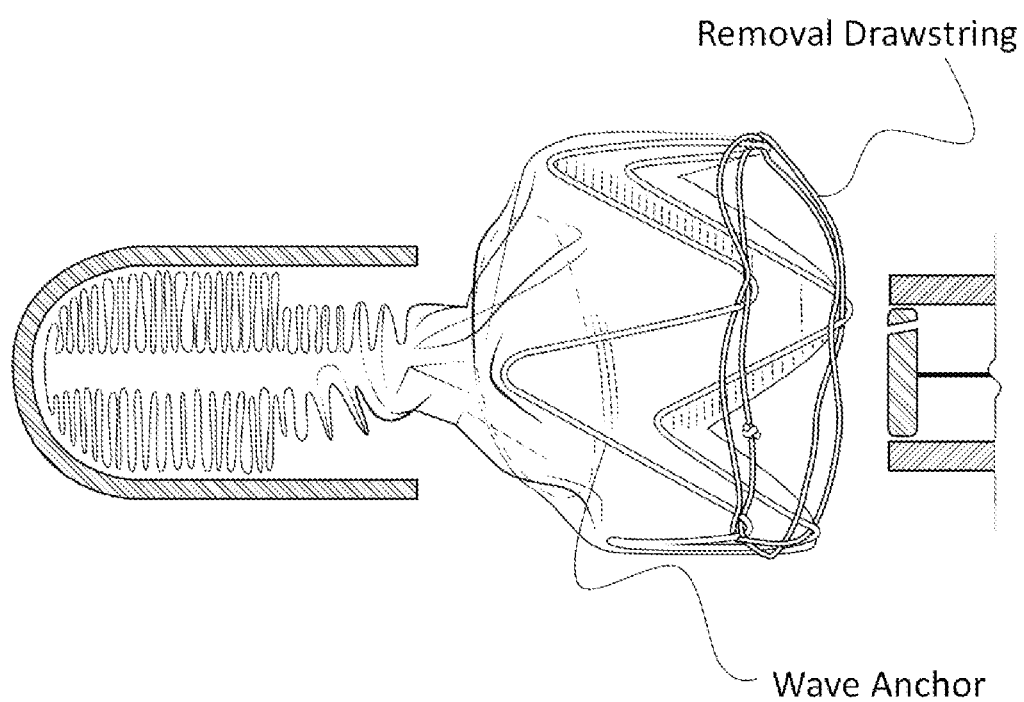
FIG. 19 is a cross-sectional view of the gastrointestinal implant after deployment from the proximal capsule. The majority of the sleeve remains within the distal cap as the anchor is expanded.
Figure 20:
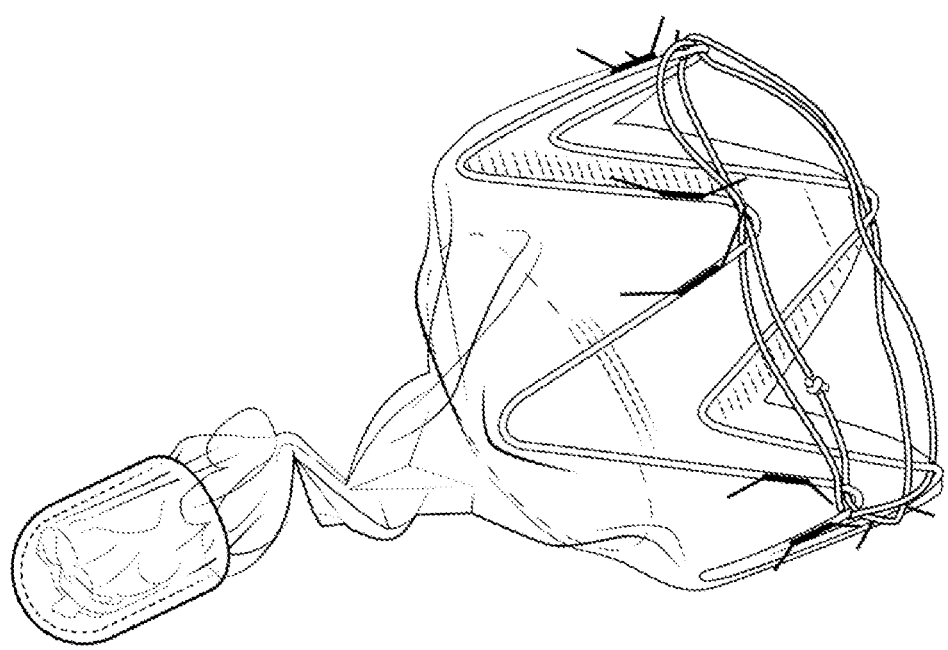
FIG. 20 is a photograph of an exemplary gastrointestinal implant after deployment from the proximal capsule. A portion of the sleeve is within the distal cap.

In some cases, upon deployment, the anchor expands radially to span the lumen of the gastrointestinal tract (e.g., the duodenum, e.g., the duodenal bulb) and exert a force thereon. Within the gastrointestinal tract (e.g., the duodenum, e.g., the duodenal bulb) the anchor can radially expand to a radius of at least 2-fold its initial radius (e.g., constrained radius; e.g., at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 10.5-fold, at least 11-fold, at least 11.5-fold, at least 12-fold, at least 13-fold, at least 14-fold, at least 15-fold, at least 16-fold, at least 17-fold, at least 18-fold, at least 19-fold, at least 20-fold, or greater). FIG. 18 shows the gastrointestinal implant in the duodenal bulb upon deployment form the proximal capsule. At this point, the sleeve remains loaded within the distal cap, while the anchor is expanded to secure the device to the gastrointestinal lumen. A cross section and photograph of a gastrointestinal implant and distal cap upon deployment is shown in FIGS. 19 and 20, respectively.

The anchor can be secured to the gastrointestinal lumen by radial expansion upon deployment (e.g., by traumatic or atraumatic means). In cases in which the anchor includes barbs, the radial expansion of the anchor can be sufficient to embed the barbs into the luminal wall of the gastrointestinal tract, thereby securing the anchor and the remainder of the gastrointestinal implant to the luminal wall of the gastrointestinal tract (e.g., at the duodenum). In some cases, the outward radial force is sufficient to secure the anchor in place without barbs. In some cases, a transpyloric element of the gastrointestinal implant supports the anchor to secure the gastrointestinal implant in position. For example, a flange may be secured to a luminal wall proximal to the pyloric sphincter, e.g., after full or partial retrieval of the delivery catheter and proximal capsule. Accordingly, methods of the present invention include attaching the flange to a proximally oriented luminal surface proximal to the pyloric orifice of a subject (e.g., a human patient), such as a proximal surface of the pyloric sphincter or antral surface of the stomach. The region to which the flange is attached will depend on subject anatomy and/or flange design (e.g., the outer diameter of the flange and/or the shape of the flange).

Figure 21:
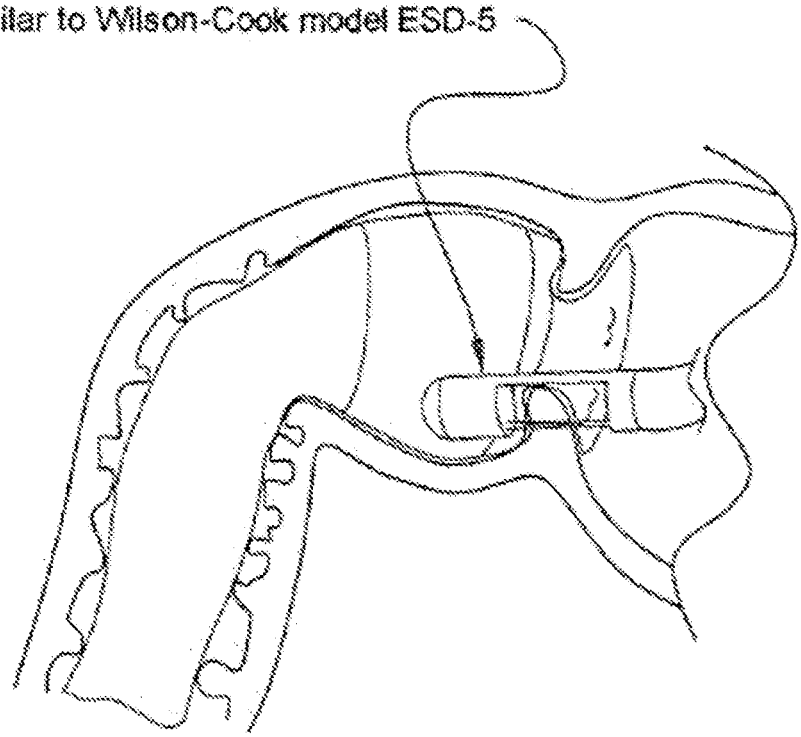
FIG. 21 is a drawing of a flanged gastrointestinal implant of the invention being implanted in a gastrointestinal tract by endoscopic suturing.

A flange can be attached to a proximally oriented luminal surface (e.g., a pyloric sphincter or the antral surface of the stomach) by transmission of a distal force from an attachment element to the proximally oriented luminal surface. For example, the distal force can be directed (e.g., endoscopically) to an attachment element, such as a suture or a staple, to secure the flange to the luminal wall (e.g., by sequentially puncturing the flange and luminal wall, or by threading an eyelet or similar opening in the flange to access the luminal wall). One embodiment of a method of attaching the flange to a proximal surface of the pyloric sphincter is illustrated by FIG. 21, showing suturing by an endoscopic suturing device similar to Wilson-Cook model ESD-5. Additionally or alternatively, any suitable method of securing a film, liner, or membrane to a tissue can be used.

After deployment of any embodiment of the gastrointestinal implant, the delivery catheter and proximal capsule can be retrieved from the gastrointestinal tract at any point following deployment of the gastrointestinal implant. In some embodiments of the methods of delivery described herein, the delivery catheter and proximal capsule are retrieved immediately upon deployment of the gastrointestinal implant.

In some embodiments, the methods of the invention further include allowing peristalsis to extend the elongate distal portion of the gastrointestinal implant (e.g., the sleeve). In some embodiments, peristalsis "takes hold" of the distal cap and forces it distally as it would with ingested material. Additionally, distal passage of a fluid (e.g., fluid flowing due to peristaltic forces) may help to extend the elongate distal portion of the gastrointestinal implant (e.g., the sleeve). In this case, the fluid can be endogenous (e.g., chyme and/or other endogenous fluids) and/or exogenous (e.g., a liquid infused by a practitioner). Exogenous fluids can be infused to accelerate elongation of the sleeve and/or to monitor proper elongation and positioning of the sleeve. Accordingly, in some embodiments, the fluid is a liquid mixture of saline and a contrast medium. Examples of suitable contrast mediums include a fluorescent material, a radiopaque material, or a contrast medium commonly used for intravenous urography (e.g., preparations of diatrizoate sodium and diatrizoate meglumine). The liquid can be a mixture of about 75% saline and about 25% RENOGRAFIN™ (available from Bracco Diagnostics, Inc. Corporation, East Princeton, N.J.). In some embodiments, at least 100 milliliters of exogenous fluid are infused (e.g., at least 150 milliliters, at least 200 milliliters, at least 250 milliliters, at least 300 milliliters, at least 350 milliliters, at least 400 milliliters, at least 500 milliliters, or more). Exogenous fluids can be infused through an inner catheter lumen as part of the delivery system (e.g., through a lumen of the delivery catheter). Alternatively, exogenous fluids can be infused through a separate system. Optionally, an endoscope is positioned across the pylorus and a fluid containing a contrast agent is directed into the duodenum to confirm patency of the gastrointestinal implant (e.g., sleeve).

Methods of Treatment

Further provided herein are methods of treatment using a gastrointestinal implants assembled or delivered using any of the aforementioned methods. Metabolic disorders treatable by such methods include type 2 diabetes, non-alcoholic steatohepatitis (NASH), non-alcoholic fatty liver disease (NAFLD), obesity, and related comorbidities thereof. Any of the gastrointestinal implants described above, delivered by any suitable method described above, can be used to treat a metabolic disorder.

Gastrointestinal implants of the invention have been shown to provide negative feedback within the enteric and/or nervous systems, reduced fat digestion, and reduced desire for food. Reduced fat digestion occurs because the sleeve delays the mixing of bile and pancreatic juices with chyme from the stomach until after the chyme leaves the sleeve. Reduced desire for food may occur because the sleeve reduces hormonal release from the duodenum. Additionally, providing poorly digested food to distal portions of the intestine, such as to the ileum, can trigger hormones that reduce appetite. Thus, such gastrointestinal implants can be used for treatment of various metabolic disorders (e.g., type 2 diabetes, NASH, NAFLD, and obesity) characterized by aberrant physiological response to ingested food, such as the incretin effect.

Placement of the gastrointestinal implant device may result in ingested food not digesting in a normal manner and modification of normal triggering of gut hormones. These hormones result in several physiology changes that impact hunger and digestion. Gut hormones that can be modified by devices of the invention include peptide YY (PYY), cholecystokinin (CCK) and ghrelin.

As under-digested food enters the ileum or distal part of the small intestine, PYY is released. PYY has been shown to have a direct effect on appetite, reducing it when released. Undigested food in the ileum indicates that too much food has been ingested. Thus, dependent on the length of the sleeve, the gastrointestinal implant can promote deposition of undigested or partially digested food to the distal bowel. Therefore, the placement of a sleeve in the intestine promotes the delivery of undigested food to the ileum, which in turn promotes the release of PYY and reduces appetite in humans.

The hormone CCK is released when food contacts the duodenum. CCK triggers the release of bile from the gallbladder. Therefore, placing a sleeve in the duodenum reduces the release of CCK and thus reduces bile output resulting in reduction in the digestion of food.

Some ghrelin is released when food contacts the duodenum. Ghrelin has been shown to be a factor in the control of appetite. Gastrointestinal implants of the invention can reduce ghrelin output and thereby reduce appetite due to the bypass of the duodenum.

Type 2 diabetes is a disease of obesity that occurs when patients cannot adequately use the insulin they produce. Usually, it is not that the patient cannot make enough insulin, but rather that the patients body cannot effectively use the insulin produced. A particularly dangerous result of type 2 diabetes is that blood sugar spikes after a meal. This is called post-prandial hyperglycemia. This spike in blood glucose causes cardiovascular and microvascular damage. One class of drugs used to control post-prandial hyperglycemia is the alpha-glucosidase inhibitors. These work by reducing the breakdown and absorption of carbohydrates to sugars. The gastrointestinal implant has a similar function because it reduces bile and delays the breakdown and absorption of the carbohydrates, which are normally readily absorbed in the duodenum, but are less likely to be absorbed in the jejunum and ileum. Therefore, type 2 diabetes can be controlled by placing a sleeve in the proximal intestine to delay the digestion of carbohydrates which reduces post-prandial hyperglycemia.

The gastrointestinal implant device can be used to reduce type 2 diabetes symptoms by bypassing all or a portion of the duodenum. Following gastric bypass surgery, patients commonly experience complete reversal of type 2 diabetes. While the exact mechanism of this remarkable effect is not understood, the clinical result is reported in a high percentage of cases. Since the gastrointestinal implant devices describe herein provides equivalent blockage of duodenal processes, a similar effect is elicited but without the trauma of surgery.

In the method of using the gastrointestinal implant for treating diabetes, placement of the anchor within the duodenum allows the pylorus to operate normally. The length of the sleeve may be reduced to mimic the duodenum bypass. The sleeve may extends to just below the ligament of Treitz but may not extend further into the jejunum, thus allowing absorption to occur in the jejunum.

EXAMPLES

Example 1: Preparation of the Delivery System for Use

The following example provides an exemplary process for preparing a delivery system of the present invention for use in delivering a gastrointestinal implant (e.g., a gastrointestinal sleeve, e.g., ENDOBARRIER®).

FIG. 3 shows an unassembled delivery system. The gastrointestinal implant shown is a gastrointestinal sleeve having a proximal anchor and a distal sleeve, shown here in its extended configuration. A central extrusion is provided to allow the catheter to pass over a guidewire for easy access to the pylorus for placement of the gastrointestinal implant. In this embodiment, the central extrusion extends proximally past the trifucate and distally through the capsule, creating a lumen that runs the length of the catheter. Alternatively, the central extrusion can extend distally past the capsule, but proximally exit the catheter between the capsule and the trifurcate, such that the lumen is only partially as long as the catheter, as shown in FIG. 4. In this embodiment, the central extrusion would be either flush with the main catheter extrusion, or a removable lumen. FIG. 5 shows a close-up view of the distal end of the catheter, attached to the proximal capsule, through which the central extrusion passes. In this embodiment, the distal cap has a central hole through which the central extrusion passes.

To pack the gastrointestinal sleeve into the container assembly, the anchor was inserted within the proximal capsule, and the sleeve was gently bunched up around the central extrusion, as shown in FIG. 6. Next, the distal cap was inserted into the distal end of the sleeve such that the proximal ~¼ inch of the distal cap was positioned within the lumen of the distal ~¼ inch of the sleeve, as shown in FIG. 7. A soft tip swab was then used to gently pack the sleeve into the distal cap, ensuring the distal ~¼ inch of the sleeve remains around the outer circumference of the proximal end of the distal cap, as shown in FIG. 8. When the sleeve was almost completely packed, the distal cap was pushed over the distal end of the proximal capsule using friction to hold the sleeve in place. The distal ~¼ inch of the sleeve remained slightly exposed but was mostly covered by the distal cap, providing a layer between the distal cap and the proximal capsule, as shown in FIG. 9. The distal length of the central extrusion can be trimmed to be nearly flush with the soft cap, e.g., to prevent trauma after the distal cap has been pushed onto the proximal capsule.

Example 2: Exemplary Delivery of a Gastrointestinal Implant

Individuals who are clinically diagnosed with obesity and/or type 2 diabetes and can benefit from medical intervention are identified as potential candidates for the receipt of a gastrointestinal implant. For example, potential candidates are between 18 and 65 years of age with a body mass index (BMI) greater than 30 kg/m$^2$, and may or may not have related comorbidities (e.g., hypertension, hyperlipidemia, NASH, or NAFLD). A simplified delivery system for use with ENDOBARRIER® GI Liners includes a catheter, a liner (including a sleeve and an anchor), and a soft cap. A skilled operator may use a conventional endoscope inserted transorally through a subjects' esophagus, through the stomach, and through the pylorus, such that the distal end of the endoscope is located within the duodenum. The operator viewing the images captured by endoscope may rely on visual confirmation that the distal end of endoscope has reached the duodenum. The endoscope is then used to place a guidewire. The endoscope is removed while leaving the guide wire in place, in a process known as "guidewire exchange." A catheter tracks over the guidewire until the cap/capsule is across the pylorus. Tracking may occur through a central lumen that passes through the soft cap and part or all of the catheter, or through offset rails on the capsule. The locking wire is used to prevent premature delivery of the GI Liner. Then, the locking wire is retracted to free the GI Liner Sutures to allow the GI Liner and cap to be ejected simultaneously. The cap and GI Liner are ejected from the capsule simultaneously into the duodenal bulb. The majority of the GI Liner sleeve is still packed into the soft cap; peristalsis will take hold of the cap and sleeve and slowly fully extend the sleeve. The soft cap will pass naturally. Once the GI Liner and cap are ejected, the catheter is removed. An endoscope may be reinserted and used to both examine the placement of the GI Liner as well as to flush the device ensure stability and to try and establish patency of the GI Liner lumen.

Previous delivery systems have included an inner catheter to advance the sleeve, a (releasable) ball coupled to the distal end of the catheter, and have required six or seven steps to deploy the liner. Simplified delivery systems of the present invention eliminate the need for a ball and an inner catheter. The simplified delivery system can deliver a liner with the following three steps: (1) Accessing the pylorus and pushing the capsule into the duodenal bulb, with registry marks on the capsule indicating location of the capsule that can be seen via endoscope; (2) Releasing the locking wire, the locking wire preventing premature plunger activation; and (3) Plunging out (e.g., ejecting) the anchor and sleeve. An optional fourth step includes flushing the sleeve out distally using exogenous fluid.

The simplified delivery systems of the present invention shorten delivery time from about half an hour (using previous delivery systems) to approximately 2-6 minutes. Shortened delivery times can omit the need for an anesthetic or allow for conscious sedation of the patient during the delivery process. As the liner is left to extend by peristaltic action of the intestine, fluoroscopy may not be required. Fluoroscopy was previously used to make sure that the ball was fully extended into the intestine and to make sure that the sleeve was not everted into the anchor. Without the use of fluoroscopy, delivery procedures could be carried out in an outpatient environment and procedure costs could be greatly reduced. Additional advantages of the simplified delivery system include easier training for use by clinicians, easier manufacturing of the devices, and less needed follow-up in the field. Due to the packaging of the sleeve within the silicone cap, simplified delivery systems can have a longer shelf life as the sleeve can be less prone to sticking upon itself. Because the cap provides additional space for the storage of the folded sleeve, the sleeve is not as tightly compressed as in prior delivery systems.

OTHER EMBODIMENTS

All publications, patents, and patent applications mentioned in this specification are herein incorporated by reference to the same extent as if each independent publication or patent application was specifically and individually indicated to be incorporated by reference. In the event of a conflicting definition between this and any reference incorporated herein, the definition provided herein applies.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims.

Other embodiments are within the claims.

What is claimed is:

1. A delivery system for placing a gastrointestinal implant in a gastrointestinal tract of a patient, the delivery system comprising:
    (a) a delivery catheter comprising a lumen;
    (b) a container assembly at the distal portion of the delivery catheter, the container assembly comprising a proximal capsule and a distal cap removably attachable thereto; and
    (c) a gastrointestinal implant comprising: (i) a sleeve configured to carry fluid from its proximal end to its distal end; and (ii) an anchor connected to the sleeve at or near its proximal end, the anchor configured to secure the proximal end of the sleeve within the gastrointestinal tract;
    wherein the gastrointestinal implant is configured to fit within the container assembly such that the anchor fits within the proximal capsule and a portion of the sleeve fits within the distal cap and
    wherein the container assembly further comprises an anchor locking mechanism within the proximal capsule.

2. The delivery system of claim 1, wherein the container assembly further comprises an ejection mechanism.

3. The delivery system of claim 1, wherein the anchor is configured to be positioned distal to the patient's pylorus.

4. A method of positioning a gastrointestinal implant in a patient, the method comprising the steps of:
    (a) providing a container assembly containing a gastrointestinal implant, the gastrointestinal implant comprising a proximal anchor and an elongate distal portion, wherein the container assembly comprises:
        (i) a proximal capsule containing the proximal portion of the gastrointestinal implant,
        (ii) a distal cap containing all or part of the elongate distal portion; and
        (iii) an anchor locking mechanism within the proximal capsule;
    (b) directing the container assembly into the patient's gastrointestinal tract;
    (c) securing the proximal anchor to a luminal wall of the gastrointestinal tract; and
    (d) allowing peristalsis to extend the elongate distal portion;
    thereby positioning the gastrointestinal implant.

5. The method of claim 4, wherein step (c) is initiated by ejecting the gastrointestinal implant and the distal cap from the proximal capsule.

6. A method of positioning a gastrointestinal implant in a patient, the method comprising the steps of:
    (a) providing a container assembly containing a gastrointestinal implant, the gastrointestinal implant comprising a proximal anchor and an elongate distal portion, wherein the container assembly comprises:
        (i) a proximal capsule containing the proximal portion of the gastrointestinal implant,
        (ii) a distal cap containing all or part of the elongate distal portion; and
        (iii) an anchor locking mechanism within the proximal capsule;
    (b) directing the container assembly into the patient's gastrointestinal tract;
    (c) ejecting the proximal anchor from the proximal capsule while the elongate distal portion is retained within the distal cap; and
    (d) allowing:
        (i) the proximal anchor to secure to a luminal wall of the gastrointestinal tract; and
        (ii) peristalsis to extend the elongate distal portion;
    thereby positioning the gastrointestinal implant in the patient.

7. The method of claim 6, wherein step (b) is performed using a delivery catheter.

8. The method of claim 6, wherein the container assembly further comprises an ejection mechanism.

* * * * *

UNITED STATES PATENT AND TRADEMARK OFFICE
CERTIFICATE OF CORRECTION

| | | |
|---|---|---|
| PATENT NO. | : 11,318,008 B2 | Page 1 of 1 |
| APPLICATION NO. | : 16/073652 | |
| DATED | : May 3, 2022 | |
| INVENTOR(S) | : Cote et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 153 days.

Signed and Sealed this
Eleventh Day of February, 2025

Coke Morgan Stewart
*Acting Director of the United States Patent and Trademark Office*